(12) United States Patent
Suzuki et al.

(10) Patent No.: US 9,447,240 B2
(45) Date of Patent: Sep. 20, 2016

(54) POLYIMIDE PRECURSOR MODIFIED WITH DICARBOXYLIC ACID ANHYDRIDE, IMIDIZED POLYIMIDE AND LIQUID CRYSTAL ALIGNING AGENT USING IT

(75) Inventors: Hideo Suzuki, Funabashi (JP); Takahiro Noda, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 240 days.

(21) Appl. No.: 14/114,409

(22) PCT Filed: Apr. 27, 2012

(86) PCT No.: PCT/JP2012/061426
§ 371 (c)(1),
(2), (4) Date: Nov. 19, 2013

(87) PCT Pub. No.: WO2012/147939
PCT Pub. Date: Nov. 1, 2012

(65) Prior Publication Data
US 2014/0066590 A1 Mar. 6, 2014

(30) Foreign Application Priority Data

Apr. 28, 2011 (JP) ................................. 2011-101814

(51) Int. Cl.
| | | |
|---|---|---|
| G02F 1/1337 | (2006.01) |
| B32B 27/28 | (2006.01) |
| C08G 73/10 | (2006.01) |
| C07D 301/03 | (2006.01) |
| C07D 303/12 | (2006.01) |
| C07D 307/00 | (2006.01) |
| C07D 493/18 | (2006.01) |
| C07D 493/22 | (2006.01) |

(52) U.S. Cl.
CPC ............. *C08G 73/10* (2013.01); *C07D 493/18* (2013.01); *C07D 493/22* (2013.01); *C08G 73/101* (2013.01); *C08G 73/1014* (2013.01); *G02F 1/133723* (2013.01)

(58) Field of Classification Search
None
See application file for complete search history.

(56) References Cited

U.S. PATENT DOCUMENTS 5,914,385 A  6/1999  Hayashi et al.

FOREIGN PATENT DOCUMENTS

| GB | 788123 A | * 12/1957 | ........... C07D 303/38 |
|---|---|---|---|
| JP | 59-166530 A | 9/1984 | |
| JP | 60-156682 A | * 8/1985 | ........... C07D 303/38 |
| JP | 60-156692 A | 8/1985 | |
| JP | 2-223916 A | 9/1990 | |
| JP | 2-287324 A | 11/1990 | |
| JP | 4-281427 A | 10/1992 | |
| JP | 5-43687 A | 2/1993 | |
| JP | 9-208698 A | 8/1997 | |
| JP | 10-46151 A | 2/1998 | |
| JP | 10-104633 A | 4/1998 | |
| JP | 10-333153 A | 12/1998 | |
| JP | 2007-11221 A | 1/2007 | |

OTHER PUBLICATIONS

Derwent Abstract of JP 60-156692 A (no date).*
JP Abstract of JP 60-156682 A (no date).*
Derwent Abstract of JP 60-156682 A (no date).*
Moss et al. "Further Rearrangements of Diepoxycyclohexanes: Formation of Acetyldihydroxycyclopentane Derivatives" (1996).*
International Search Report Issued Jul. 13, 2012 in PCT/JP12/061426 Filed Apr. 27, 2012.
Bernd Giese, "Bestimmung der sterischen Wechselwirkung in offenen und verbrückten Norbornanderivaten" Chemische Berichte, vol. 107 (3), 1974, pp. 808-818 (with English Abstract).

* cited by examiner

*Primary Examiner* — Michael J Feely
(74) *Attorney, Agent, or Firm* — Oblon, McClelland, Maier & Neustadt, L.L.P.

(57) ABSTRACT

To provide a polyimide precursor and/or polyimide which has an excellent solubility in various organic solvents, and with which a liquid crystal alignment film can be obtained which is excellent in a rubbing resistance and which is hardly deteriorated even by irradiation with backlight.

A polyimide precursor having its terminal amino group modified with at least one alicyclic epoxydicarboxylic acid anhydride selected from the group consisting of compounds of the formulae [1] and [2], or a polyimide obtained by imidizing it:

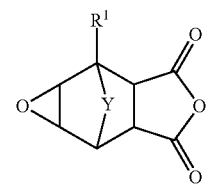

[1]

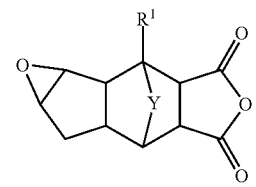

[2]

R1 = H, or —X¹—X²—X³ wherein Y is a $C_{1-2}$ alkylene or an oxygen atom, and $R^1$ is a hydrogen atom or an organic group represented by —$X^1$—$X^2$—$X^3$, wherein $X^1$ is a single bond or —$CH_2$—, $X^2$ is a single bond or —O—, and $X^3$ is a $C_{1-20}$ alkyl group, a $C_{1-20}$ haloalkyl group or a $C_{1-20}$ alkyl group containing a cyano group.

18 Claims, No Drawings

POLYIMIDE PRECURSOR MODIFIED WITH DICARBOXYLIC ACID ANHYDRIDE, IMIDIZED POLYIMIDE AND LIQUID CRYSTAL ALIGNING AGENT USING IT

TECHNICAL FIELD

The present invention relates to a polyimide precursor having its terminal modified with a side chain-substituted alicyclic epoxydicarboxylic acid anhydride, an imidized polyimide, and particularly, a liquid crystal aligning agent using it.

BACKGROUND ART

In a liquid crystal display device, a liquid crystal alignment film has a role to align liquid crystal in a certain direction. At present, a principal liquid crystal alignment film industrially utilized is prepared by applying a polyimide type liquid crystal aligning agent comprising a solution of a polyamide acid (also called a polyamic acid) as a polyimide precursor or a polyimide obtained by imidizing the polyamide acid, to a substrate to form a film. Further, in the case of parallel alignment or tilt alignment of the liquid crystal relative to the substrate surface, a surface orientation treatment by rubbing is further carried out after film formation.

In order to improve the display properties of a liquid crystal display device, the structure of the polyamic acid or the polyimide is changed variously and optimized, resins differing in the properties are blended, or additives are added, to improve the liquid crystal alignment property, to control the pretilt angle, or to improve electric properties, etc., and for further improvement in the display properties, various techniques have been proposed. For example, Patent Document 1 proposes to employ a polyimide resin having a specific repeating structure in order to obtain a high voltage retention. Further, Patent Document 2 proposes to shorten the time till the residual image disappears, by using a soluble polyimide having a nitrogen atom in addition to the imide group, against the image retention phenomenon.

Further, the liquid crystal alignment film also has a role to impart a certain angle of inclination (pretilt angle) to the liquid crystal, and to impart the pretilt angle, a diamine containing side chains, etc., have been proposed, and impartment of the pretilt angle becomes an important object in development of a liquid crystal alignment film (Patent Documents 3 to 6).

Further, a liquid crystal alignment film has been desired such that the film is less likely to be peeled or scraped, when rubbing treatment is carried out as a process to impart uniaxial alignment property of liquid crystal molecules to a polyimide film (Patent Documents 7 to 9).

In recent years, along with the progress in high performance of a liquid crystal display device, increase in the area, energy saving of a display device, etc., a liquid crystal display device is used in various environments, and properties required for a liquid crystal alignment film are also diversified in a high level. Particularly, along with an increase in the size of a display, light and heat of the backlight tend to be intense, and development of a material resistant to deterioration by light or heat has been desired.

PRIOR ART DOCUMENTS

Patent Documents

Patent Document 1: JP-A-2-287324
Patent Document 2: JP-A-10-104633
Patent Document 3: JP-A-02-223916
Patent Document 4: JP-A-04-281427
Patent Document 5: JP-A-05-043687
Patent Document 6: JP-A-10-333153
Patent Document 7: JP-A-10-46151
Patent Document 8: JP-A-2007-11221

DISCLOSURE OF INVENTION

Technical Problem

Under these circumstances, the object of the present invention is to provide a polyimide precursor modified with an alicyclic epoxydicarboxylic acid anhydride having a side chain substituent, or a polyimide obtained by imidizing it, suitably used for a liquid crystal aligning agent with which a liquid crystal alignment film can be obtained, which has favorable rubbing resistance, which can impart a pretilt angle depending on the structure, and which is hardly deteriorated even by irradiation with backlight.

Solution to Problem

The present inventors have conducted extensive studies to achieve the above object and as a result, established a novel dicarboxylic acid anhydride having a side chain substituent in an oxabicyclo[2.2.1] heptane ring having an alicyclic structure, and its production process, and further succeeded in obtaining a polyimide precursor and/or a polyimide having its terminal chemically modified with the dicarboxylic acid anhydride.

With the polyimide precursor and/or polyimide having its terminal chemically modified, which has an excellent solubility in various organic solvents, a polyimide polymer which is soluble even in an organic solvent having a low boiling point, can be obtained. Accordingly, it can be suitably used as a protective material for a liquid crystal display device or a semiconductor, an electronic material such as an insulating material, and a material for optical communication such as a light waveguide. Particularly when it is used for a liquid crystal aligning agent, an excellent liquid crystal alignment film can be obtained, which is less likely to be scraped at the time of rubbing treatment, which is hardly deteriorated even by irradiation with backlight, and which can impart a high pretilt angle to the liquid crystal depending on the structure.

That is, the present invention provides the following.

(1) A polyimide precursor having its terminal amino group modified with at least one alicyclic epoxydicarboxylic acid anhydride selected from the group consisting of compounds of the formulae [1]and [2], or a polyimide obtained by imidizing it:

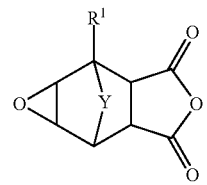

[A]

-continued

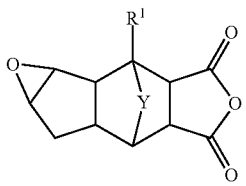

R1 = H, or —X¹—X²—X³ wherein Y is a $C_{1-2}$ alkylene or an oxygen atom, and $R^1$ is a hydrogen atom or an organic group represented by —X¹—X²—X³, wherein $X^1$ is a single bond or —$CH_2$—, $X^2$ is a single bond or —O—, and $X^3$ is a $C_{1-20}$ alkyl group, a $C_{1-20}$ haloalkyl group or a $C_{1-20}$ alkyl group containing a cyano group.

(2) The polyimide precursor or polyimide obtained by imidizing it according to the above (1), wherein the alicyclic epoxydicarboxylic acid anhydride is at least one compound selected from compounds represented by the following formula [A] to [C]:

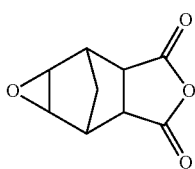

[A]

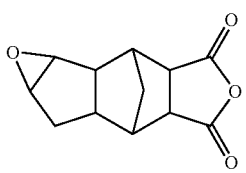

[B]

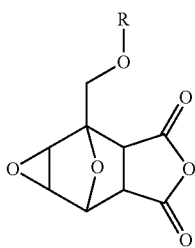

[C]

wherein R is a $C_{1-20}$ alkyl group, a $C_{1-20}$ haloalkyl group or a $C_{1-20}$ alkyl group containing a cyano group.

(3) A method for producing a polyimide precursor having its terminal amino group modified or a polyimide obtained by imidizing it, which comprises reacting at least one alicyclic epoxydicarboxylic acid anhydride selected from the group consisting of compounds of the formulae [1] and [2] as defined in the above (1) with a polyimide precursor having an amino group at its terminal or a polyimide obtained by imidizing it.

(4) The method for producing a polyimide precursor having its terminal amino group modified or a polyimide obtained by imidizing it according to the above (3), wherein a polyimide precursor having from 50 to 100% of terminal amino groups to the total number of terminal groups derived from a tetracarboxylic acid and terminal groups derived from a diamine, or a polyimide obtained by imidizing it, is used.

(5) A liquid crystal aligning agent containing at least one of the polyimide precursor and the polyimide obtained by imidizing it according to the above (1) or (2).

(6) A liquid crystal alignment film obtained by using the liquid crystal aligning agent as defined in the above (5).

(7) A liquid crystal display device having the liquid crystal alignment film as defined in the above (6).

(8) A compound represented by the formula [1]:

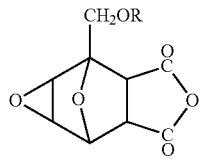

[1]

wherein R is a $C_{1-20}$ alkyl group, a $C_{1-20}$ haloalkyl group or a $C_{1-20}$ alkyl group containing a cyano group.

(9) The compound according to the above (8), wherein R is a n-tetradecyl group.

(10) A compound represented by the formula [2]:

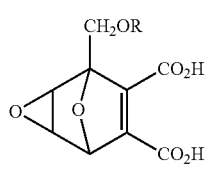

[2]

wherein R is a $C_{1-20}$ alkyl group, a $C_{1-20}$ haloalkyl group or a $C_{1-20}$ alkyl group containing a cyano group.

(11) The compound according to the above (10), wherein R is a n-tetradecyl group.

(12) A compound represented by the formula [3]:

[3]

wherein R is a $C_{1-20}$ alkyl group, a $C_{1-20}$ haloalkyl group or a $C_{1-20}$ alkyl group containing a cyano group.

(13) The compound according to the above (12), wherein R is a n-tetradecyl group.

(14) A process for producing a compound represented by the formula [1], which comprises reacting furfuryl alcohol with a substituted alkyl halide represented by the formula [4] in the presence of a base to obtain a compound represented by the formula [5], reacting the compound represented by the formula [5] with acetylenedicarboxylic acid to obtain a compound represented by the formula [6], oxidizing the compound represented by the formula [6] to obtain a compound represented by the formula [3], reducing the compound represented by the formula [3] to obtain a compound represented by the formula [2], followed by dehydration with a dehydrating agent:

RX  [4]

wherein R is as defined above, and X is a halogen atom;

[5]

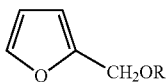

wherein R is as defined above;

[6]

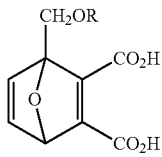

wherein R is as defined above;

[3]

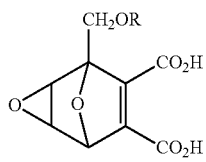

wherein R is as defined above;

[2]

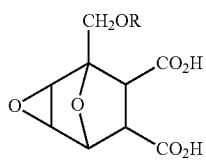

wherein R is as defined above; and

[1]

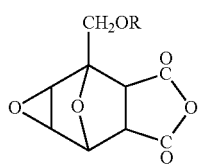

wherein R is as defined above.
(15) The production process according to the above (14), wherein R is a n-tetradecyl group.

Advantageous Effects of Invention

According to the polyimide precursor and/or polyimide having its terminal chemically modified with the alicyclic epoxydicarboxylic acid anhydride of the present invention, a polyimide polymer which has an excellent solubility in various organic solvents and which is soluble even in an organic solvents having a low boiling point is provided.

This polyimide polymer is suitably used, for example, for a protective material for a liquid crystal display device or a semiconductor, an electronic material such as an insulating material, or a material for optical communication such as a light waveguide. Particularly when it is used for a liquid crystal aligning agent, it is possible to obtain an excellent liquid crystal alignment film with high reliability, which is less likely to be scraped at the time of rubbing treatment, and of which a decrease in the voltage retention by backlight, heat or the like is small, due to a crosslinked structure in the polyimide chain by epoxy groups contained.

Description of Embodiments

[Side Chain-Substituted alicyclic epoxydicarboxylic acid anhydride]

The side chain-substituted alicyclic epoxydicarboxylic acid anhydride of the present invention is represented by the following formula [1] or [2]:

[1]

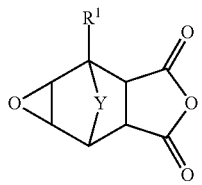

[2]

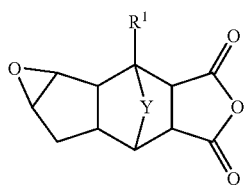

$R_1 = H$, or $—X^1—X^2—X^3$ wherein Y is a $C_{0-2}$ alkylene or an oxygen atom, and $R^1$ is a hydrogen atom or an organic group represented by $—X^1—X^2—X^3$, wherein $X^1$ is a single bond or $—CH_2—$, $X^2$ is a single bond or $—O—$, and $X^3$ is a $C_{1-20}$ alkyl group, a $C_{1-20}$ haloalkyl group or a $C_{1-20}$ alkyl group containing a cyano group.

Now, the present invention will be described in further detail.

In the following, n represents normal, i iso, s secondary, t tertiary and c cyclo.

In the above formulae [1] and [2], as $X^3$ in $R^1$, the $C_{1-20}$ alkyl group may be linear, branched or cyclic, and for the purpose of obtaining a higher pretilt angle, $R^1$ is preferably a $C_{2-20}$ alkyl group, more preferably a $C_{5-20}$ alkyl group, further preferably a $C_{8-18}$ alkyl group.

On the other hand, in the case of use for a liquid crystal aligning agent for an IPS liquid crystal display device for which no pretilt angle is required, $R^1$ is preferably non-substituted i.e. a hydrogen atom, and it is variously selected depending upon the application of the liquid crystal display.

Among the above compounds of the formulae, preferred are compounds having the following structures:

[A]

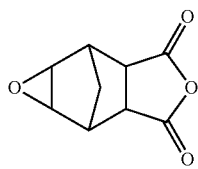

-continued

[B]

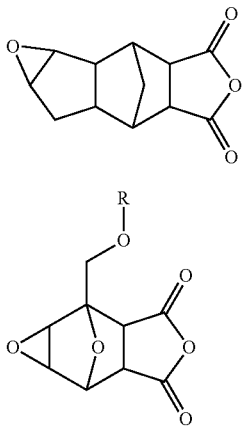

[C]

wherein R is a $C_{1-20}$ alkyl group, a $C_{1-20}$ haloalkyl group or a $C_{1-20}$ alkyl group containing a cyano group.

For example, 3,4-epoxy-tricyclo[5.2.1.0$^{2,6}$]decane-8,9-dicarboxylic acid anhydride which is a compound of the above formula [2] wherein Y is a carbon atom, and $R^1$ is a hydrogen atom, can be produced in accordance with a method disclosed in JP-A-60-156692.

Further, 5,6-epoxy-1-substituted oxymethyl-7-oxabicyclo[2.2.1]heptane-2,3-dicarboxylic acid anhydride (hereinafter referred to as EAOA) which is a compound of the above formula [1] wherein Y is an oxygen atom, $X^1$ in $R^1$ is —$CH_2$—, $X^2$ is an oxygen atom and $X^3$ is an alkyl side chain, is produced by the following series of reaction scheme.

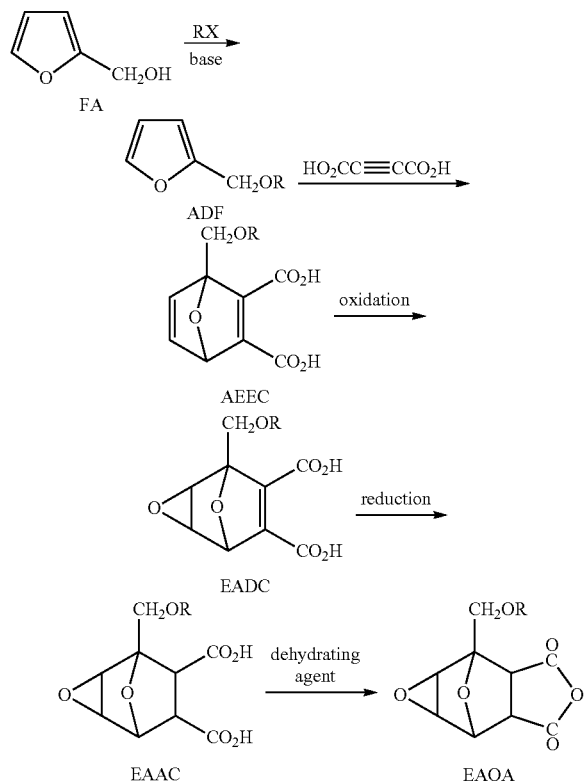

wherein R is as defined above, and X is a halogen atom.

That is, in the first step, furfuryl alcohol (FA) is reacted with an alkyl halide in the presence of a base to obtain a 2-substituted oxymethylfuran (ADF).

In the second step, ADF is reacted with acetylenedicarboxylic acid to obtain 1-substituted oxymethyl-7-oxabicyclo[2.2.1]hepta-2,5-diene-2,3-dicarboxylic acid (AEEC).

In the third step, AEEC is oxidized to obtain 2,3-epoxy-1-substituted oxymethyl-7-oxabicyclo[2.2.1]hepta-2,5-diene-5,6-dicarboxylic acid (EADC).

In the fourth step, EADC is reduced to obtain 2,3-epoxy-1-substituted oxymethyl-7-oxabicyclo[2.2.1]heptane-5,6-dicarboxylic acid (EAAC).

In the fifth step, EAAC is converted to EAOA with a dehydrating agent.

Now, the respective steps will be described in detail.

As furfuryl alcohol (FA) as the material in the first step, a commercially available product may be used as it is.

The substituted alkyl halide as the other material may be a $C_{1-20}$ alkyl halide, a $C_{1-20}$ haloalkyl halide or a $C_{2-20}$ cyanoalkyl halide.

The halogen atom as X may be a fluorine atom, a chlorine atom, a bromine atom or a iodine atom.

Specifically, the alkyl halide wherein R is $C_{1-20}$ alkyl group may, for example, be iodomethane, iodoethane, iodopropane, iodobutane, iodopentane, iodohexane, iodoheptane, iodooctane, iodononane, iododecane, bromobutane, bromopentane, bromohexane, bromoheptane, bromooctane, bromononane, bromodecane, bromoundecane, bromododecane, bromotridecane, bromotetradecane, bromopentadecane, bromohexadecane, bromoheptadecane, bromooctadecane, bromononadecane or bromoeicosane.

The haloalkyl halide wherein R is a $C_{1-20}$ haloalkyl group may, for example, be $CF_3I$, $CF_3CH_2I$, $CF_3CF_2I$, $CF_3(CH_2)_2I$, $CF_3(CF_2)_2I$, $CF_3CF_2CH_2I$, $CF_3(CF_2)_3I$, $CF_3CF_2(CH_2)_2I$, $CF_3(CF_2)_4I$, $CF_3(CF_2)_2(CH_2)_2I$, $CF_3(CF_2)_5I$, $CF_3(CF_2)_3(CH_2)_2I$, $CF_3(CF_2)_6I$, $CF_3(CF_2)_4(CH_2)_2I$, $CF_3(CF_2)_7I$, $CF_3(CF_2)_5(CH_2)_2I$, $CF_3(CF_2)_8I$, $CF_3(CF_2)_6(CH_2)_2I$, $CF_3(CF_2)_9I$, $CF_3(CF_2)_7(CH_2)_2I$, $CF_3(CF_2)_{10}I$, $CF_3(CF_2)_8(CH_2)_2I$, $CF_3(CF_2)_{11}I$, $CF_3(CF_2)_{12}I$, $CF_3(CF_2)_{13}I$, $CF_3(CF_2)_{14}I$, $CF_3(CF_2)_{15}I$, $CF_3(CF_2)_{16}I$, $CF_3(CF_2)_{17}I$, $CF_3(CF_2)_{18}I$ or $CF_3(CF_2)_{19}I$.

The cyanoalkyl halide wherein R is a $C_{1-20}$ alkyl group containing a cyano group may, for example, be $BrCH_2CN$, $Br(CH_2)_2CN$, $Br(CH_2)_3CN$, $Br(CH_2)_4CN$, $Br(CH_2)_5CN$, $Br(CH_2)_6CN$, $Br(CH_2)_7CN$, $Br(CH_2)_4C(CH_3)_2CN$, $Br(CH_2)_8CN$, $Br(CH_2)_9CN$, $Br(CH_2)_{10}CN$, $Br(CH_2)_{11}CN$, $Br(CH_2)_{12}CN$, $Br(CH_2)_{13}CN$, $Br(CH_2)_{14}CN$, $Br(CH_2)_{15}CN$, $Br(CH_2)_{16}CN$, $Br(CH_2)_{17}CN$, $Br(CH_2)_{18}CN$ or $Br(CH_2)_{19}CN$.

The amount of use of the alkyl halide is preferably from 2 to 3 molar times, more preferably from 2 to 2.5 molar times relative to FA.

The base is preferably a metal hydride, and may, for example, be specifically lithium hydride, sodium hydride or potassium hydride, and is particularly preferably sodium hydride.

The amount of its use is preferably from 2 to 3 molar times, more preferably from 2 to 2.5 molar times relative to FA.

The reaction solvent is preferably N,N-dimethylformamide (DMF), tetrahydrofuran (THF), 1,4-dioxane or the like. The amount of use of the reaction solvent is preferably from 2 to 20 parts by mass, more preferably from 3 to 15 parts by mass per 1 part by mass of furfuryl alcohol.

Further, in a case where the alkyl halide is a bromide, a metal iodide may be added. The metal iodide may be sodium iodide or potassium iodide.

The amount of use of the iodide is preferably from 0.1 to 3 molar times, more preferably from 0.2 to 2.5 molar times relative to FA.

The reaction temperature is preferably from about −30 to 200° C., more preferably from 0 to 150° C.

After the reaction, the solvent is removed to concentrate the reaction liquid, ethyl acetate is added, and the reaction liquid is acidified with e.g. an aqueous hydrochloric acid solution, and an organic layer is isolated by liquid separation, which is concentrated to obtain an oily crude product. The crude product is purified by e.g. silica gel column chromatography to obtain the desired ADF.

As acetylenedicarboxylic acid used for the Diels-Alder reaction in the second step, a commercially available product may be used as it is. The amount of its use is preferably from 1 to 1.5 molar times, more preferably from 1 to 1.2 molar times relative to ADF.

It is preferred to use a reaction solvent, and the reaction solvent may, for example, be N,N-dimethylformamide (DMF), tetrahydrofuran (THF) or 1,4-dioxane. The amount of use of the reaction solvent is preferably from 2 to 20 parts by mass, more preferably from 3 to 15 parts by mass.

The reaction temperature is preferably from about 0 to 200° C., more preferably from 0 to 150° C.

After the reaction, the reaction liquid is concentrated, and a mixed liquid of n-hexane or n-heptane with ethyl acetate is added to the obtained crude product, followed by heating for dissolution, and cooling with ice, whereupon crystals of the desired AEEC will precipitate.

The purity of the crude crystals can be improved by repeatedly carrying out recrystallization using a mixed liquid of n-hexane or n-heptane with ethyl acetate.

As an oxidizing agent to be used in the oxidation method in the third step, oxygen molecules, hydrogen peroxide, an organic peroxide or the like may be used. Particularly, when an organic peroxide is used, peracetic acid is preferred, whereby a high yield is achieved under moderate reaction conditions. The amount of its use is preferably from 1 to 3 molar times, more preferably from 1.5 to 2 molar times relative to AEEC.

Further, it is possible to let disodium hydrogen phosphate coexist as a stabilizer for a product. Its amount of use is preferably from 0.01 to 1 molar time, more preferably from 0.05 to 0.5 molar time relative to AEEC.

The reaction solvent may, for example, be acetic acid or 1,4-dioxane. Its amount of use is preferably from 2 to 20 parts by mass, more preferably from 3 to 15 parts by mass relative to AEEC.

The reaction temperature is preferably from about 0 to 150° C., more preferably from 0 to 100° C.

After the reaction, the reaction mixture is concentrated, and ethyl acetate is added to the obtained crude product for dissolution, followed by washing with water, whereupon an oily crude product of the desired EADC is obtained. Further, acetonitrile is added to the oily crude product and heated, whereupon insoluble matters are separated to form a slurry. Then, the slurry is subjected to filtration with celite, and the filtrate is concentrated and vacuum dried to obtain an oily product of the desired EADC.

As the reduction method in the fourth step, various common reduction methods which convert a double bond to a single bond may be applicable. For example, (1) reduction with a metal and a metal salt, (2) reduction with a metal hydride, (3) reduction with a metal hydrogen complex compound, (4) reduction with diborane and a substituted borane, (5) reduction with hydrazine, (6) reduction with diimide, (7) reduction with a phosphorus compound, (8) electrolytic reduction or (9) catalytic reduction may, for example, be mentioned.

Among them, the most practical method is (9) catalytic reduction method. The catalytic reduction method which can be employed in the present invention is as follows.

In the catalytic reduction method, as a reducing agent, preferably hydrogen gas is used, and a catalyst and a solvent are preferably used.

The catalyst may, for example, be a group 8 element palladium, ruthenium, rhodium, platinum, nickel, cobalt, iron, or a group 1 element copper in the periodic table. Such metals may be used alone or as a multicomponent metal combined with another element. The form of the catalyst may, for example, be a simple substance of each metal, a Raney catalyst, a catalyst supported on diatomaceous earth, alumina, zeolite, carbon or another carrier, or a complex catalyst.

Specifically, palladium/carbon, ruthenium/carbon, rhodium/carbon, platinum/carbon, palladium/alumina, ruthenium/alumina, rhodium/alumina, platinum/alumina, reduced nickel, reduced cobalt, Ranay nickel, Ranay cobalt, Ranay copper, copper oxide, copper chromate, chlorotris (triphenylphosphine)rhodium, chlorohydridotris(triphenylphosphine)ruthenium, dichlorotris(triphenylphosphine)ruthenium or hydridocarbonyltris(triphenylphosphine)iridium may, for example, be mentioned. Among them, particularly preferred is palladium/carbon, ruthenium/carbon or the like.

The amount of use of the catalyst is preferably from 0.1 to 30 mass %, particularly preferably from 0.5 to 20 mass % relative to the substrate, in the form of a 5 mass % metal supported catalyst.

As the solvent, an alcohol represented by methanol, ethanol or propanol, an ether represented by dioxane, tetrahydrofuran or dimethoxyethane, or an ester represented by ethyl acetate or propyl acetate may, for example, be used.

Its amount of use is preferably within a range of from 1 to 50 times by mass, particularly preferably from 3 to 20 times by mass relative to the material.

The hydrogen pressure is preferably within a range of from normal pressure to 10 MPa (100 kg/cm$^2$), particularly preferably from normal pressure to 3 MPa (30 kg/cm$^2$).

The reaction temperature is preferably within a range of from 0 to 150° C., particularly preferably from 10 to 100° C. The reduction reaction may be traced by the hydrogen absorption amount.

After the reaction, the catalyst is removed by filtration, and the filtrate is concentrated and vacuum dried to obtain an oily product of the desired EAAC.

As the dehydrating method in the fifth step, (a) an aliphatic carboxylic acid anhydride method, (b) a formic acid and p-toluene sulfonic acid method, or (c) an azeotropic method by an aromatic hydrocarbon may, for example, be mentioned. Among them, it is preferred to employ (a) aliphatic carboxylic acid anhydride method, which is simple in operation, which is economically efficient and with which the desired product can be obtained with a higher yield.

The aliphatic carboxylic acid anhydride may, for example, be acetic anhydride or propionic anhydride, and is preferably acetic anhydride in view of economical efficiency.

The amount of addition of the aliphatic carboxylic acid anhydride is preferably from 2 to 30 molar times, more preferably from 3 to 20 molar times relative to the material EAAC.

The dehydrating reaction is preferably carried out in the presence of a reaction solvent. In this step, the reaction liquid is colored along with the progress of the reaction, and the crystals of the product are likely to be colored, however, by the presence of a reaction solvent, coloring of the reaction liquid can be reduced and as a result, coloring of the product can be suppressed.

The reaction solvent may, for example, be an aromatic hydrocarbon compound such as benzene, toluene, xylene, ethylbenzene or cumene, or acetonitrile. Among them, toluene is preferred.

The amount of addition of the reaction solvent is preferably from 1 to 30 times by mass, more preferably from 3 to 20 times by mass relative to the material EAAC.

Further, the reaction may be carried out in the presence of activated carbon for the purpose of decoloring. In such a case, the amount of use of activated carbon is preferably from 1 to 100 mass %, more preferably from 3 to 50 mass % relative to the material EAAC.

The reaction temperature is usually preferably from about 50 to 150° C., and considering shortening of the time until completion of the reaction, it is suitably from 60 to 130° C.

The reaction time correlates with the reaction temperature, and is usually preferably from 10 minutes to 5 hours, more preferably from 15 minutes to 3 hours.

After the dehydrating reaction, the reaction liquid is cooled to room temperature (25° C.) and subjected to filtration with celite, and the obtained filtrate is concentrated, to obtain an oily product of the desired EAOA. In a case where unreacted EAAC remains, the purity of the desired product can be increased by repeatedly carrying out the dehydrating reaction.

[Polyimide Precursor and Polyimide to be Modified]

In the present invention, a polyimide precursor or a polyimide modified with the above side chain-substituted alicyclic epoxydicarboxylic acid anhydride is obtained. In the present invention, the polyimide precursor means a polyamic acid and/or a polyamic acid ester. The polyamic acid is obtained by reaction of a diamine component with a tetracarboxylic acid dianhydride. The polyamic acid ester is obtained by reacting a diamine component with a tetracarboxylic acid diester dichloride in the presence of a base or by reacting a tetracarboxylic acid diester with a diamine in the presence of appropriate condensing agent and base.

Further, the polyimide is obtained by subjecting the polyamic acid to cyclodehydration or by subjecting the polyamic acid ester to heat cyclization. Any of the polyamic acid, the polyamic acid ester and the polyimide is useful as a polymer to obtain a liquid crystal alignment film.

The diamine component to be used is not particularly limited, and its specific examples are as follows. The alicyclic diamine may, for example, be 1,4-diaminocyclohexane, 1,3-diaminocyclohexane, 4,4'-diaminodicyclohexylmethane, 4,4'-diamino-3,3'-dimethyldicyclohexylamine or isophoronediamine.

The aromatic diamine may, for example, be o-phenylenediamine, m-phenylenediamine, p-phenylenediamine, 2,4-diaminotoluene, 2,5-diaminotoluene, 3,5-diaminotoluene, 1,4-diamino-2-methoxybenzene, 2,5-diamino-p-xylene, 1,3-diamino-4-chlorobenzene, 3,5-diamino benzoic acid, 1,4-diamino-2,5-dichlorobenzene, 4,4'-diamino-1,2-diphenylethane, 4,4'-diamino-2,2'-dimethylbibenzyl, 4,4'-diaminodiphenylmethane, 3,3'-diaminodiphenylmethane, 3,4'-diaminodiphenylmethane, 4,4'-diamino-3,3'-dimethyldiphenylmethane, 2,2'-diaminostilbene, 4,4'-diaminostilbene, 4,4'-diamino diphenyl ether, 3,4'-diamino diphenyl ether, 4,4'-diamino diphenyl sulfide, 4,4'-diamino diphenyl sulfone, 3,3'-diamino diphenyl sulfone, 4,4'-diaminobenzophenone, 1,3-bis(3-aminophenoxy)benzene, 1,3-bis(4-aminophenoxy)benzene, 1,4-bis(4-aminophenoxy)benzene, 3,5-bis(4-aminophenoxy)benzoic acid, 4,4'-bis(4-aminophenoxy)biphenyl, 2,2-bis[(4-aminophenoxy)methyl]propane, 2,2-bis[4-(4-aminophenoxy)phenyl]hexafluoropropane, 2,2-bis[4-(4-aminophenoxy)phenyl]propane, bis[4-(3-aminophenoxy)phenyl]sulfone, bis[4-(4-aminophenoxy)phenyl]sulfone, 1,1-bis(4-aminophenyl)cyclohexane, α,α'-bis(4-aminophenyl)-1,4-diisopropylbenzene, 9,9-bis(4-aminophenyl)fluorene, 2,2-bis(3-aminophenyl)hexafluoropropane, 2,2-bis(4-aminophenyl)hexafluoropropane, 4,4'-diaminodiphenylamine, 2,4-diaminodiphenylamine, 1,8-diaminonaphthalene, 1,5-diaminonaphthalene, 1,5-diaminoanthraquinone, 1,3-diaminopyrene, 1,6-diaminopyrene, 1,8-diaminopyrene, 2,7-diaminofluorene, 1,3-bis(4-aminophenyl)tetramethyldisiloxane, benzidine, 2,2'-dimethylbenzidine, 1,2-bis(4-aminophenyl)ethane, 1,3-bis(4-aminophenyl)propane, 1,4-bis(4-aminophenyl)butane, 1,5-bis(4-aminophenyl)pentane, 1,6-bis(4-aminophenyl)hexane, 1,7-bis(4-aminophenyl)heptane, 1,8-bis(4-aminophenyl)octane, 1,9-bis(4-aminophenyl)nonane, 1,10-bis(4-aminophenyl)decane, 1,3-bis(4-aminophenoxy)propane, 1,4-bis(4-aminophenoxy)butane, 1,5-bis(4-aminophenoxy)pentane, 1,6-bis(4-aminophenoxy)hexane, 1,7-bis(4-aminophenoxy)heptane, 1,8-bis(4-aminophenoxy)octane, 1,9-bis(4-aminophenoxy)nonane, 1,10-bis(4-aminophenoxy)decane, di(4-aminophenyl)propane-1,3-dioate, di(4-aminophenyl)butane-1,4-dioate, di(4-aminophenyl)pentane-1,5-dioate, di(4-aminophenyl)hexane-1,6-dioate, di(4-aminophenyl)heptane-1,7-dioate, di(4-aminophenyl)octane-1,8-dioate, di(4-aminophenyl)nonane-1,9-dioate, di(4-aminophenyl)decane-1,10-dioate, 1,3-bis[4-(4-aminophenoxy)phenoxy]propane, 1,4-bis[4-(4-aminophenoxy)phenoxy]butane, 1,5-bis[4-(4-aminophenoxy)phenoxy]pentane, 1,6-bis[4-(4-aminophenoxy)phenoxy]hexane, 1,7-bis[4-(4-aminophenoxy)phenoxy]heptane, 1,8-bis[4-(4-aminophenoxy)phenoxy]octane, 1,9-bis[4-(4-aminophenoxy)phenoxy]nonane or 1,10-bis[4-(4-aminophenoxy)phenoxy]decane.

The aromatic/aliphatic diamine may, for example, be 3-aminobenzylamine, 4-aminobenzylamine, 3-amino-N-methylbenzylamine, 4-amino-N-methylbenzylamine, 3-aminophenethylamine, 4-aminophenethylamine, 3-amino-N-methylphenethylamine, 4-amino-N-methylphenethylamine, 3-(3-aminopropyl)aniline, 4-(3-aminopropyl)aniline, 3-(3-methylaminopropyl)aniline, 4-(3-methylaminopropyl)aniline, 3-(4-aminobutyl)aniline, 4-(4-aminobutyl)aniline, 3-(4-methylaminobutyl)aniline, 4-(4-methylaminobutyl)aniline, 3-(5-aminopentyl)aniline, 4-(5-aminopentyl)aniline, 3-(5-methylaminopentyl)aniline, 4-(5-methylaminopentyl)aniline, 2-(6-aminonaphthyl)methylamine, 3-(6-aminonaphthyl)methylamine, 2-(6-aminonaphthyl)ethylamine or 3-(6-aminonaphthyl)ethylamine.

The heterocyclic diamine may, for example, be 2,6-diaminopyridine, 2,4-diaminopyridine, 2,4-diamino-1,3,5-triazine, 2,7-diaminodibenzofuran, 3,6-diaminocarbazole, 2,4-diamino-6-isopropyl-1,3,5-triazine or 2,5-bis(4-aminophenyl)-1,3,4-oxadiazole.

The aliphatic diamine may, for example, be 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,3-diamino-2,2-dimethylpropane, 1,6-diamino-2,5-dimethylhexane, 1,7-diamino-2,5-dimethylheptane, 1,7-diamino-4,4-dimethylheptane, 1,7-diamino-3-methylheptane, 1,9-diamino-5-methylheptane, 1,12-diaminododecane, 1,18-diaminooctadecane or 1,2-bis(3-aminopropoxy)ethane.

A diamine compound having in its side chain an alkyl group, a fluorine-containing alkyl group, an aromatic ring, an aliphatic ring, a heterocyclic ring or a macrocyclic substituent comprising it may be used in combination. Specifically, diamines of the following formulae [DA1] to [DA26] may be mentioned.

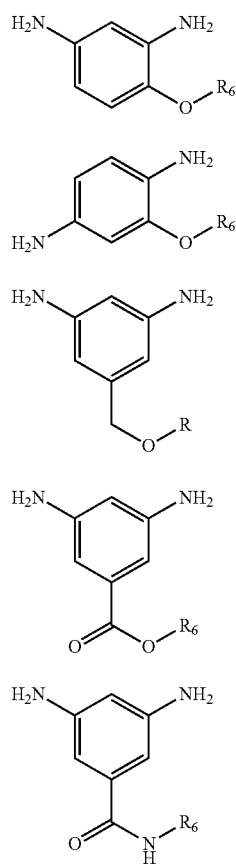

In the formulae [DA1] to [DA5], $R_6$ is a $C_{1-22}$ alkyl group or a fluorine-containing alkyl group.

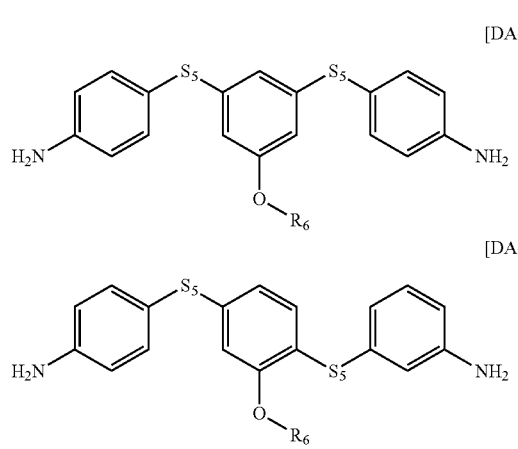

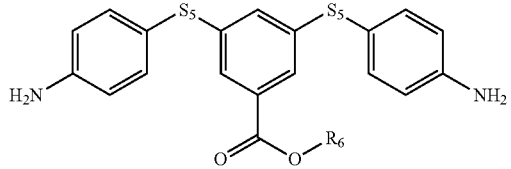

In the formulae [DA6] to [DA9], $S_5$ is —COO—, —OCO—, —CONH—, —NHCO—, —CH$_2$—, —O—, —CO— or —NH—, and $R_6$ is a $C_{1-22}$ alkyl group or fluorine-containing alkyl group.

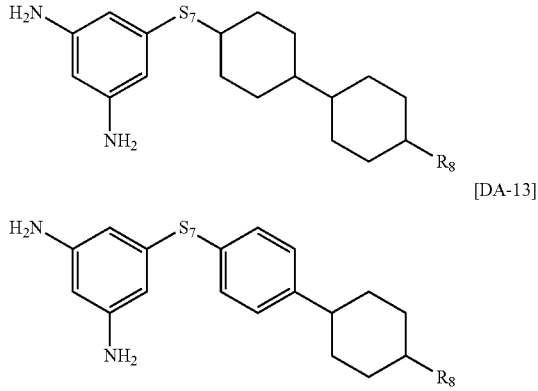

In the formulae [DA10] and [DA11], $S_6$ is —O—, —OCH$_2$—, —CH2O—, —COOCH$_2$— or —CH$_2$OCO—, and $R_7$ is a $C_{1-22}$ alkyl group, an alkoxy group, a fluorine-containing alkyl group or a fluorine-containing alkoxy group.

[DA-14]

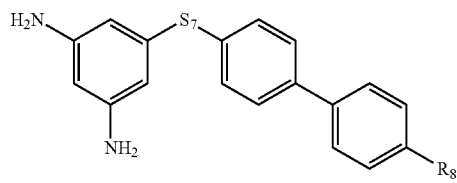

[DA-17]

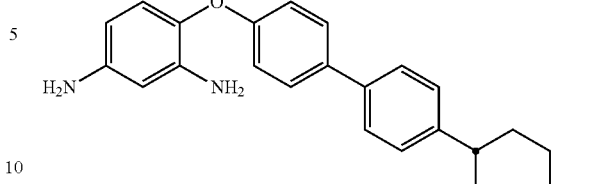

In the formulae [DA12] to [DA14], $S_7$ is —COO—, —OCO—, —CONH—, —NHCO—, —COOCH$_2$—, —CH$_2$OCO—, —CH$_2$O—, —OCH$_2$— or —CH$_2$—, and $R_8$ is a $C_{1-22}$ alkyl group, an alkoxy group, a fluorine-containing alkyl group or a fluorine-containing alkoxy group.

[DA-18]

[DA-15]

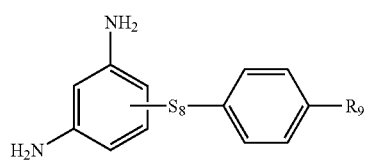

[DA-19]

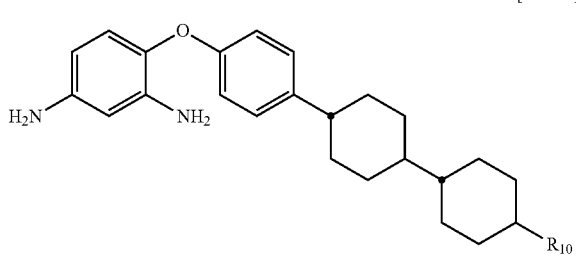

[DA-16]

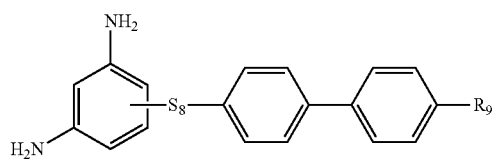

[DA-20]

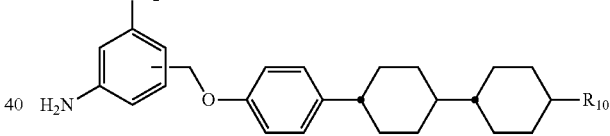

In the formulae [DA15] and [DA16], $S_8$ is —COO—, —OCO—, —CONH—, —NHCO—, —COOCH$_2$—, —CH$_2$OCO—, —CH$_2$O—, —OCH$_2$—, —CH$_2$—, —O— or —NH—, and $R_9$ is a fluorine group, a cyano group, a trifluoromethane group, a nitro group, an azo group, a formyl group, an acetyl group, an acetoxy group or a hydroxy group.

In the formulae [DA17] to [DA20], $R_{10}$ is a $C_{3-12}$ alkyl group, and each 1,4-cyclohexylene is a trans isomer in terms of cis-trans isomerism.

[DA-17]

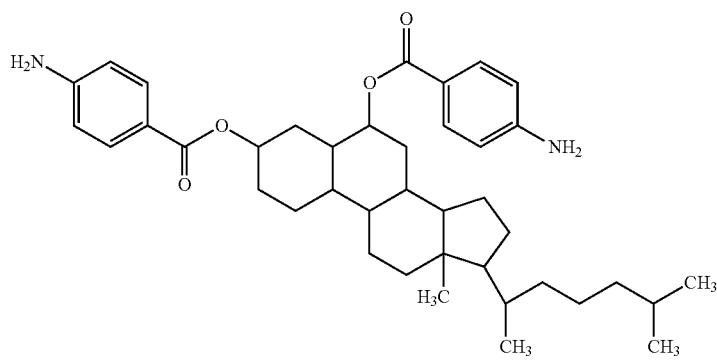

[DA-18]
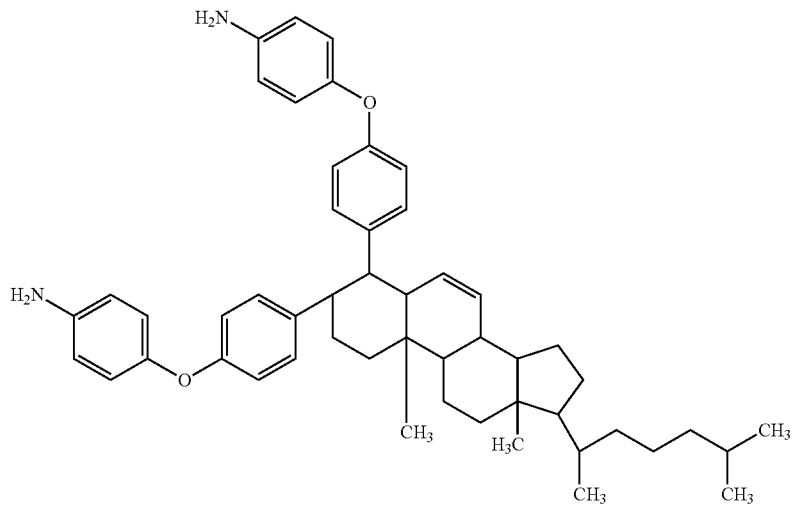
[DA-19] [DA-20]
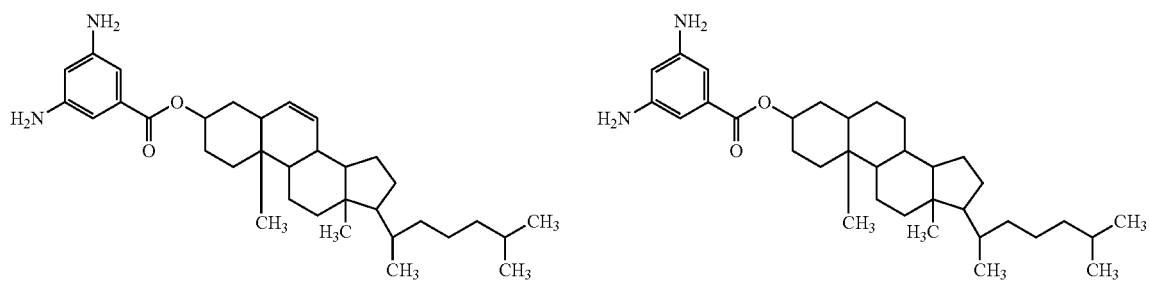
[DA-21] [DA-22]
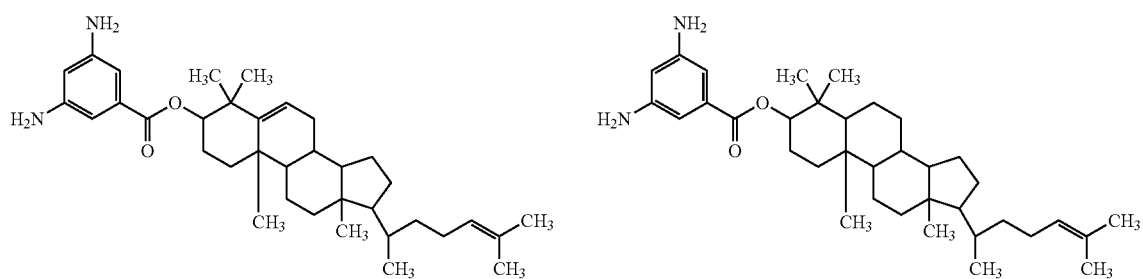
[DA-23] [DA-24]
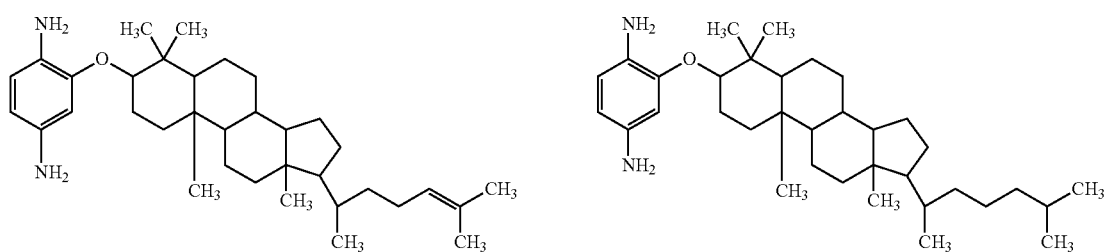

-continued
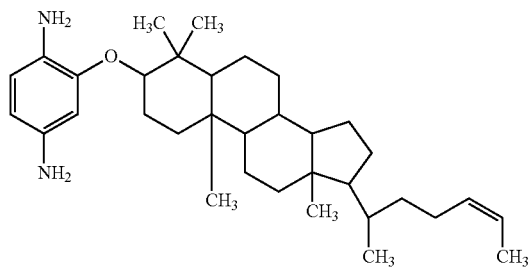
[DA-25]
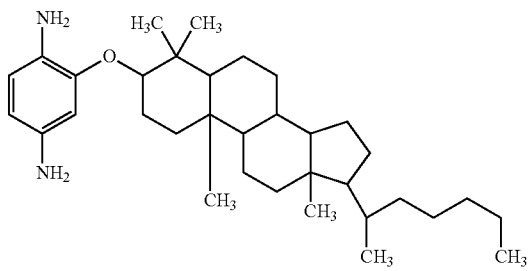
[DA-26]
Further, the following diamines may be used in combination.
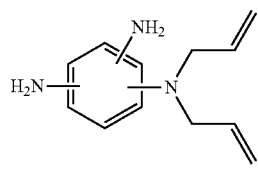
[DA-27]
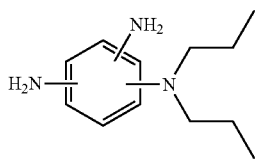
[DA-28]
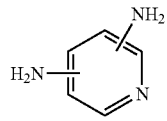
[DA-29]
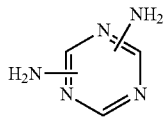
[DA-30]
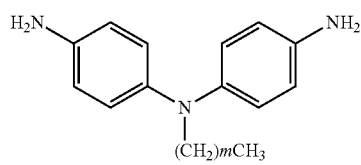
[DA-31]
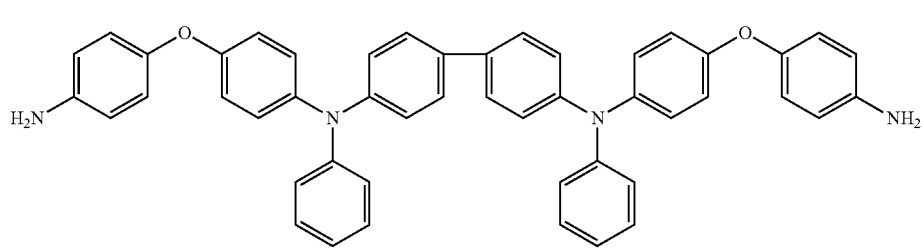
[DA-32]
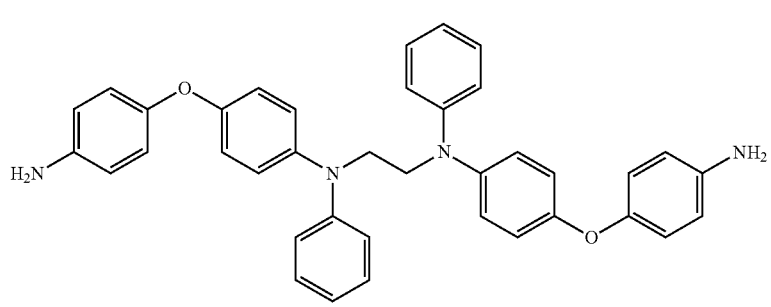
[DA-33]

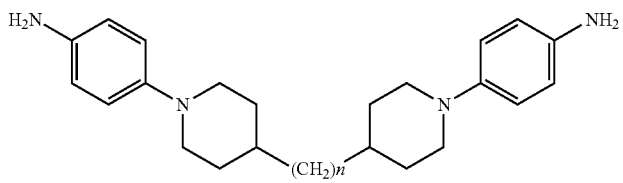

[DA-34]

In the formula [DA31], m is an integer of from 0 to 3, and in the formula [DA34], n is an integer of from 1 to 5.

In a case where a diamine of e.g. [DA-27] or [DA-28] is used, a liquid crystal alignment film obtainable from a liquid crystal aligning agent using the obtained polymer can improve a voltage retention (also referred to as VHR) of a liquid crystal display device. Further, use of a diamine of [DA-29] to [DA-34] is effective to reduce the accumulated charge of a liquid crystal display device.

Further, as a diamine compound, a diaminosiloxane as represented by the following formula [DA-35] may, for example, be mentioned:

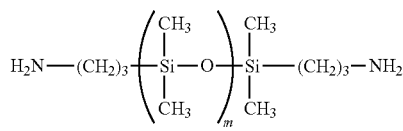

[DA-35]

In the formula [DA-35], m is an integer of from 1 to 10.

The above diamine compounds may be used alone or as a mixture of two or more depending upon the properties when a liquid crystal alignment film is obtained, such as the liquid crystal alignment property, the voltage retention property and the accumulated charge.

The tetracarboxylic acid dianhydride to be reacted with the diamine component to obtain the polyimide precursor is not particularly limited. Its specific examples are as follows.

The tetracarboxylic acid dianhydride having an alicyclic structure or an aliphatic structure may, for example, be 1,2,3,4-cyclobutanetetracarboxylic acid dianhydride, 1,2-dimethyl-1,2,3,4-cyclobutanetetracarboxylic acid dianhydride, 1,3-dimethyl-1,2,3,4-cyclobutanetetracarboxylic acid dianhydride, 1,2,3,4-tetramethyl-1,2,3,4-cyclobutanetetracarboxylic acid dianhydride, 1,2,3,4-cyclopentanetetracarboxylic acid dianhydride, 2,3,4,5-tetrahydrofurantetracarboxylic acid dianhydride, 1,2,4,5-cyclohexanetetracarboxylic acid dianhydride, 3,4-dicarboxy-1-cyclohexylsuccinic acid dianhydride, 3,4-dicarboxy-1,2,3,4-tetrahydro-1-naphthalenesuccinic acid dianhydride, 1,2,3,4-butanetetracarboxylic acid dianhydride, bicyclo[3.3.0] octane-2,4,6,8-tetracarboxylic acid dianhydride, 3,3',4,4'-dicyclohexyltetracarboxylic acid dianhydride, 2,3,5-tricarboxycyclopentyl acetic acid dianhydride, cis-3,7-dibutylcycloocta-1,5-diene-1,2,5,6-tetracarboxylic acid dianhydride, tricyclo[4.2.1.0$^{2,5}$]nonane-3,4,7,8-tetracarboxylic acid-3,4:7,8-dianhydride, hexacyclo [6.6.0.1$^{2,7}$.0$^{3,6}$.1$^{9,14}$.0$^{10,13}$]hexadecane-4,5,11,12-tetracarboxylic acid-4,5:11,12-dianhydride or 4-(2,5-dioxotetrahydrofuran-3-yl)-1,2,3,4-tetrahydronaphthalene-1,2-dicarboxylic acid anhydride.

Further, in addition to the tetracarboxylic acid dianhydride having an alicyclic structure or an aliphatic structure, an aromatic tetracarboxylic acid dianhydride is preferably used, whereby the liquid crystal alignment property will be improved, and the accumulated charge of a liquid crystal cell can be reduced.

The aromatic tetracarboxylic acid dianhydride may, for example, be pyromellitic acid dianhydride, 3,3',4,4'-biphenyltetracarboxylic acid dianhydride, 2,2',3,3'-biphenyltetracarboxylic acid dianhydride, 2,3,3',4'-biphenyltetracarboxylic acid dianhydride, 3,3',4,4'-benzophenonetetracarboxylic acid dianhydride, 2,3,3',4'-benzophenonetetracarboxylic acid dianhydride, bis(3,4-dicarboxyphenyl)ether dianhydride, bis(3,4-dicarboxyphenyl)sulfonic acid dianhydride, 1,2,5,6-naphthalenetetracarboxylic acid dianhydride or 2,3,6,7-naphthalenetetracarboxylic acid dianhydride.

The tetracarboxylic acid dialkyl ester to be reacted with the diamine component to obtain the polyamide acid ester is not particularly limited. Its specific examples are as follows.

The aliphatic tetracarboxylic acid diester may, for example, be specifically 1,2,3,4-cyclobutanetetracarboxylic acid dialkyl ester, 1,2-dimethyl-1,2,3,4-cyclobutanetetracarboxylic acid dialkyl ester, 1,3-dimethyl-1,2,3,4-cyclobutanetetracarboxylic acid dialkyl ester, 1,2,3,4-tetramethyl-1,2,3,4-cyclobutanetetracarboxylic acid dialkyl ester, 1,2,3,4-cyclopentanetetracarboxylic acid dialkyl ester, 2,3,4,5-tetrahydrofurantetracarboxylic acid dialkyl ester, 1,2,4,5-cyclohexanetetracarboxylic acid dialkyl ester, 3,4-dicarboxy-1-cyclohexylsuccinic acid dialkyl ester, 3,4-dicarboxy-1,2,3,4-tetrahydro-1-naphthalenesuccinic acid dialkyl ester, 1,2,3,4-butanetetracarboxylic acid dialkyl ester, bicyclo[3.3.0]octane-2,4,6,8-tetracarboxylic acid dialkyl ester, 3,3',4,4'-dicyclohexyltetracarboxylic acid dialkyl ester, 2,3,5-tricarboxycyclopentylacetic acid dialkyl ester, cis-3,7-dibutylcycloocta-1,5-diene-1,2,5,6-tetracarboxylic acid dialkyl ester, tricyclo[4.2.1.0$^{2,5}$]nonane-3,4,7,8-tetracarboxylic acid-3,4:7,8-dialkyl ester, hexacyclo [6.6.0.1$^{2,7}$.0$^{3,6}$.1$^{9,14}$.0$^{10,13}$]hexadecane-4,5,11,12-tetracarboxylic acid-4,5:11,12-dialkyl ester or 4-(2,5-dioxotetrahydrofuran-3-yl)-1,2,3,4-tetrahydronaphthalene-1,2-dicarboxylic acid dialkyl ester.

The aromatic tetracarboxylic acid dialkyl ester may, for example, be pyromellitic acid dialkyl ester, 3,3',4,4'-biphenyltetracarboxylic acid dialkyl ester, 2,2',3,3'-biphenyltetracarboxylic acid dialkyl ester, 2,3,3',4'-biphenyltetracarboxylic acid dialkyl ester, 3,3',4,4'-benzophenonetetracarboxylic acid dialkyl ester, 2,3,3',4'-benzophenonetetracarboxylic acid dialkyl ester, bis(3,4-dicarboxyphenyl)ether dialkyl ester, bis(3,4-dicarboxyphenyl)sulfone dialkyl ester, 1,2,5,6-naphthalenetetracarboxylic acid dialkyl ester or 2,3,6,7-naphthalenetetracarboxylic acid dialkyl ester.

The tetracarboxylic acid dianhydrides may be used alone or in combination of two or more depending upon the properties when a liquid crystal alignment film is formed, such as the liquid crystal alignment property, the voltage retention property and the accumulated charge.

To obtain the polyamide acid of the present invention by a reaction of the tetracarboxylic acid dianhydride with the diamine component, a known synthesis means may be employed. Commonly employed is a method of reacting a tetracarboxylic acid dianhydride with a diamine component in an organic solvent. The reaction of a tetracarboxylic acid dianhydride with a diamine is advantageous in that it relatively easily proceeds in an organic solvent, and that no by-product will form.

The organic solvent to be used for the reaction of the tetracarboxylic acid dianhydride with the diamine is not particularly limited so long as the formed polyamide acid is dissolved in it. Its specific examples are as follows.

N,N-dimethylformamide, N,N-dimethylacetamide, N-methyl-2-pyrrolidone, N-ethyl-2-pyrrolidone, N-methyl-caprolactam, dimethylsulfoxide, tetramethylurea, pyridine, dimethylsulfone, hexamethylsulfoxide, γ-butyrolactone, isopropyl alcohol, methoxymethylpentanol, dipentene, ethyl amyl ketone, methyl nonyl ketone, methyl ethyl ketone, methyl isoamyl ketone, methyl isopropyl ketone, methyl cellosolve, ethyl cellosolve, methyl cellosolve acetate, ethyl cellosolve acetate, butyl carbitol, ethyl carbitol, ethylene glycol, ethylene glycol monoacetate, ethylene glycol monoisopropyl ether, ethylene glycol monobutyl ether, propylene glycol, propylene glycol monoacetate, propylene glycol monomethyl ether, propylene glycol-tert-butyl ether, dipropylene glycol monomethyl ether, diethylene glycol, diethylene glycol monoacetate, diethylene glycol dimethyl ether, dipropylene glycol monoacetate monomethyl ether, dipropylene glycol monomethyl ether, dipropylene glycol monoethyl ether, dipropylene glycol monoacetate monoethyl ether, dipropylene glycol monopropyl ether, dipropylene glycol monoacetate monopropyl ether, 3-methyl-3-methoxybutyl acetate, tripropylene glycol methyl ether, 3-methyl-3-methoxybutanol, diisopropyl ether, ethyl isobutyl ether, diisobutylene, amyl acetate, butyl butyrate, butyl ether, diisobutyl ketone, methylcyclohexene, propyl ether, dihexyl ether, dioxane, n-hexane, n-pentane, n-octane, diethyl ether, cyclohexanone, ethylene carbonate, propylene carbonate, methyl lactate, ethyl lactate, methyl acetate, ethyl acetate, n-butyl acetate, propylene glycol monoethyl ether acetate, methyl pyruvate, ethyl pyruvate, methyl 3-methoxypropionate, methylethyl 3-ethoxypropionate, ethyl 3-methoxypropionate, 3-ethoxypropionic acid, 3-methoxypropionic acid, propyl 3-methoxypropionate, butyl 3-methoxypropionate, diglyme, 4-hydroxy-4-methyl-2-pentanone, 3-methoxy-N,N-dimethylpropane amide, 3-ethoxy-N,N-dimethylpropane amide or 3-butoxy-N,N-dimethylpropane amide may, for example, be mentioned. They may be used alone or as a mixture. Further, a solvent in which the polyamide acid is not dissolved may be used as mixed with the above solvent within a range where the formed polyamide acid will not precipitate.

Further, moisture in the organic solvent will inhibit the polymerization reaction and may cause hydrolysis of the formed polyamide acid, and accordingly the organic solvent is preferably one which is dehydrated and dried as far as possible.

To react the tetracarboxylic acid dianhydride with the diamine component in the organic solvent, a method of adding the tetracarboxylic acid dianhydride as it is or as dispersed or dissolved in an organic solvent, to a liquid having the diamine component dispersed or dissolved in an organic solvent with stirring, or on the contrary, a method of adding the diamine component to a liquid having the tetracarboxylic acid dianhydride dispersed or dissolved in an organic solvent, or a method of alternately adding the tetracarboxylic acid dianhydride and the diamine component may, for example, be mentioned, and any of these methods may be employed. Further, in a case where each of the tetracarboxylic acid dianhydride and the diamine component comprises a plurality of compounds, they may be reacted as mixed, the respective compounds are sequentially reacted separately, or the compounds are separately reacted to form low molecular weight products, which are mixed and reacted to obtain a high molecular weight product.

On that occasion, the polymerization temperature is optionally selected from −20 to 150° C., and is preferably from −5 to 100° C.

Further, the reaction may be carried out at an optional concentration. If the concentration is too low, a high molecular weight polymer will hardly be obtained, and if the concentration is too high, the viscosity of the reaction liquid will be too high, whereby uniform mixing will be difficult. Accordingly, the total concentration of the tetracarboxylic acid dianhydride and the diamine component in the reaction solution is preferably from 1 to 50 mass %, more preferably from 5 to 30 mass %. The reaction is carried out at a high concentration at the initial stage of the reaction, and then the organic solvent may be added.

In the polymerization reaction to produce the polyamide acid, the ratio of the total number of moles of the tetracarboxylic acid dianhydride to the total number of moles of the diamine component is preferably from 0.8 to 1.2. Like usual polycondensation reaction, the closer to 1.0 the molar ratio is, the higher the molecular weight of the polyamide acid to be formed will be.

The polyimide of the present invention is a polyimide obtained by cyclodehydration of the polyamide acid, and is useful as a polymer to obtain a liquid crystal alignment film.

In the polyimide of the present invention, the cyclodehydration degree (imidization degree) of amino acid groups is not necessarily 100%, and may optionally be adjusted depending upon the application and the purpose of use.

[Polyimide]

As a method of imidizing the polyamide acid, thermal imidization of heating a solution of the polyamide acid as it is, or catalytic imidization of adding a catalyst to a solution of the polyamide acid may be mentioned.

In the case of thermal imidization of the polyamide acid in a solution, the temperature is from 100 to 400° C., preferably from 120 to 250° C., and it is preferably carried out while water formed by the imidization reaction is discharged out of the system.

The catalytic imidization of the polyamide acid may be carried out by adding a basic catalyst and an acid anhydride to a solution of the polyamide acid, followed by stirring at from −20 to 250° C., preferably from 0 to 180° C. The amount of the basic catalyst is from 0.5 to 30 molar times, preferably from 2 to 20 molar times the amide acid groups, and the amount of the acid anhydride is from 1 to 50 molar times, preferably from 3 to 30 molar times the amide acid groups.

The basic catalyst may, for example, be pyridine, triethylamine, trimethylamine, tributylamine or trioctylamine, and among them, pyridine is preferred, which has appropriate basicity to proceed the reaction.

The acid anhydride may, for example, be acetic anhydride, trimellitic anhydride or pyromellitic anhydride, and among them, it is preferred to use acetic anhydride, whereby purification after completion of the reaction will easily be carried out.

The imidization degree by catalytic imidization may be controlled by adjusting the catalyst amount, the reaction temperature and the reaction time.

[Polyamic Acid Ester]

To synthesize the polyamic acid ester, the polyamic acid ester as one type of the precursor of the polyimide can be obtained by the reaction of a tetracarboxylic acid diester dichloride with a diamine, or by a reaction of a tetracarboxylic acid diester with a diamine in appropriate condensing agent and base. Otherwise, a polyamic acid is preliminarily polymerized, and the carboxylic acid in the amic acid is esterified utilizing a polymer reaction to obtain a polyamic acid ester.

Specifically, a tetracarboxylic acid diester dichloride and a diamine are reacted in the presence of a base and an organic solvent at from -20 to 150° C., preferably from 0 to 50° C., for from 30 minutes to 24 hours, preferably from 1 to 4 hours.

As the base, pyridine, triethylamine or 4-dimethylaminopyridine may be used, and preferred is pyridine for moderate progress of the reaction. The amount of addition of the base is preferably from 2 to 4 molar times relative to the tetracarboxylic acid diester dichloride, whereby the base will easily be removed, and a high molecular weight product will easily be obtained.

In a case where condensation polymerization is carried out in the presence of a condensing agent, triphenyl phosphite, dicyclohexylcarbodiimide, 1-ethyl-3-(3-dimethylaminopropyl)carbodiimide hydrochloride, N,N'-carbonyldiimidazole, dimethoxy-1,3,5-triazinylmethyl morpholinium, O-(benzotriazol-1-yl)-N,N,N',N'-tetramethyluronium tetrafluoroborate, O-(benzotriazol-1-yl)-N,N,N',N'-tetramethyluronium hexafluorophosphate, diphenyl (2,3-dihydro-2-thioxo-3-benzooxazolyl)phosphonate or 4-(4,6-dimethoxy-1,3,5-triazin-2-yl)4-methoxymorpholium chloride n-hydrate may, for example, be used.

In the above method of using the condensing agent, by addition of a Lewis acid as an additive, the reaction will effectively proceed. The Lewis acid is preferably a halogenated lithium such as lithium chloride or lithium bromide. The amount of addition of the Lewis acid is preferably from 0.1 to 1.0 molar time relative to (C1).

As the solvent to be used for the above reaction, the same solvent as used for polymerization of the polyamic acid may be used, and preferred is N-methyl-2-pyrrolidone or γ-butyrolactone in view of the solubility of the monomer and the polymer, and they may be used alone or as mixed. The concentration at the time of synthesis is preferably from 1 to 30 mass %, more preferably from 5 to 20 mass %, whereby the polymer is less likely to precipitate, and a high molecular weight product will easily be obtained. Further, in order to prevent hydrolysis of the tetracarboxylic acid diester dichloride, the solvent to be used for synthesis of the polyamic acid ester is preferably dehydrated as far as possible, and the reaction is preferably carried out in a nitrogen atmosphere while preventing inclusion of the air.

[Recovery of Polymer]

To recover the formed polyamide acid, polyamic acid ester or polyimide from the reaction solution of the polyamide acid, the polyamic acid ester or the polyimide, the reaction solution is poured into a poor solvent to precipitate each of them.

The poor solvent to be used for precipitation may, for example, be methanol, acetone, hexane, butyl cellosolve, heptane, methyl ethyl ketone, methyl isobutyl ketone, ethanol, toluene, benzene or water. The reaction solution is poured into the poor solvent, and the precipitated polymer is recovered by filtration, and dried under normal pressure or under reduced pressure at room temperature or with heating. Further, an operation of dissolving the precipitated and recovered polymer again in an organic solvent, and precipitating and recovering it again for from 2 to 10 times, impurities in the polymer can be reduced. The poor solvent in such a case may, for example, be an alcohol, a ketone or a hydrocarbon, and it is preferred to use three or more types of poor solvents selected from them, whereby the purification efficiency will further be improved.

The molecular weight of the polyamide acid or the polyimide contained in the liquid crystal aligning agent of the present invention is preferably from 5,000 to 1,000,000, more preferably from 10,000 to 150,000, as the weight average molecular weight measured by a GPC (gel permeation chromatography) method, considering the strength of the obtainable coating film, workability at the time of forming the coating film, and uniformity of the coating film.

[Polyimide Precursor and Polyimide having their Terminals Modified]

The above alicyclic epoxydicarboxylic acid anhydride has reactivity with an amino group, and for example, by reacting such an alicyclic epoxydicarboxylic acid anhydride with a polyimide precursor polymer such as a polyamic acid or a polyamic acid ester in which polymer terminal amino groups are present in excess, a polyimide precursor having its terminal chemically modified can be obtained.

Further, the polyimide having its terminal modified is preferably obtained by imidizing the polyimide precursor having its terminal modified. Whereas, in a case where a polyimide having its terminal modified is obtained by reacting the above alicyclic epoxydicarboxylic acid anhydride with a polyimide obtained by imidizing the polyimide precursor, the terminal amino groups are reacted with e.g. acetic anhydride used in the imidization process as a previous step, and are converted to acetylamide terminals, such being unfavorable.

In a case where the terminal of the polyimide precursor is modified with the alicyclic epoxydicarboxylic acid anhydride, the polyamic acid or the polyamic acid ester preferably have terminal amino groups in excess. That is, the proportion of amino groups reactive with the dicarboxylic acid anhydride in the polyimide precursor is preferably from 50 to 100%, particularly preferably from 80 to 100% to the total number of terminal groups derived from a tetracarboxylic acid and terminal groups derived from a diamine.

Accordingly, the proportion of the tetracarboxylic acid dianhydride to be used for polymerization to obtain the polyimide precursor is preferably lower than the diamine, and more preferably, the proportion of the tetracarboxylic acid dianhydride is preferably from 80 to 99.5 mol, particularly preferably from 90 to 99 mol per 100 mol of the diamine component.

When the alicyclic epoxydicarboxylic acid anhydride of the present invention is reacted with the terminal amino groups of the polyamic acid, the reaction will easily proceed, and accordingly the reaction conditions are not particularly limited. For example, the alicyclic epoxydicarboxylic acid anhydride is added to the polyimide precursor to be modified, and they are reacted at from −10 to 150° C., preferably from 0 to 100° C., particularly preferably at room temperature for from 1 to 100 hours, particularly for from 3 to 30 hours.

On that occasion, to promote the reaction, the reaction may be carried out in the presence of an organic base such as pyridine as the case requires.

The structure of the polyimide precursor of which the terminal is to be chemically modified is not particularly limited, however, one having higher reactivity of terminal amine is preferred. In a case where a substituent to inhibit the reaction is present in the vicinity of the terminal group, the terminal may hardly be chemically modified in some cases. Accordingly, a polyamic acid or a polyamic acid ester obtained by using a diamine having no substituent to cause steric hindrance, or a polyamic acid or a polyamic acid ester obtained by a polymerization method by which highly reactive amino groups are terminal groups, is preferably used.

<Liquid Crystal Aligning Agent>

The liquid crystal aligning agent of the present invention is a coating fluid for forming a liquid crystal alignment film and is a solution having a polymer component to form a coating film dissolved in an organic solvent. The polymer component is a resin component containing at least one polymer selected from the above polyimide precursor having its terminal modified and the polyimide obtained by imidizing the polyimide precursor. The content of the polymer component in the liquid crystal aligning agent is preferably from 1 to 20 mass %, more preferably from 3 to 15 mass %, particularly preferably from 3 to 10 mass %.

In the present invention, the above polymer component may be entirely the polyimide precursor having its terminal modified and/or the polyimide obtained by imidizing the polyimide precursor or may contain another polymer component. In such a case, the content of such another polymer component in all the polymer components is preferably from 5 to 15 mass %, more preferably from 1 to 10 mass %.

Such another polymer component may, for example, be a polyamide acid or a polyimide obtained by using a diamine compound other than the specific diamine compound, as the diamine component to be reacted with the tetracarboxylic acid dianhydride component.

The organic solvent to be used for the liquid crystal aligning agent of the present invention is not particularly limited so long as a resin component is dissolved in it. Its specific examples are as follows.

N,N-dimethylformamide, N,N-dimethylacetamide, N-methyl-2-pyrrolidone, N-methylcaprolactam, 2-pyrrolidone, N-ethylpyrrolidone, N-vinylpyrrolidone, dimethylsulfoxide, tetramethylurea, pyridine, dimethylsulfone, hexamethylsulfoxide, γ-butyrolactone, 3-methoxy-N,N-dimethylpropane amide, 3-ethoxy-N,N-dimethylpropane amide, 3-butoxy-N,N-dimethylpropane amide, 1,3-dimethyl-imidazolidinone, ethyl amyl ketone, methyl nonyl ketone, methyl ethyl ketone, methyl isoamyl ketone, methyl isopropyl ketone, cyclohexanone, ethylene carbonate, propylene carbonate, diglyme or 4-hydroxy-4-methyl-2-pentanone. They may be used alone or as mixed.

The liquid crystal aligning agent of the present invention may contain a component other than the above. Such a component may, for example, be a solvent or a compound to improve the film thickness uniformity and the surface smoothness when the liquid crystal aligning agent is applied, or a compound to improve the adhesion between the liquid crystal alignment film and the substrate.

Specific examples of a solvent (poor solvent) to improve the film thickness uniformity or the surface smoothness are as follows.

For example, a solvent having a low surface tension, such as isopropyl alcohol, methoxymethyl pentanol, methyl cellosolve, ethyl cellosolve, butyl cellosolve, methyl cellosolve acetate, ethyl cellosolve acetate, butyl carbitol, ethyl carbitol, ethyl carbitol acetate, ethylene glycol, ethylene glycol monoacetate, ethylene glycol monoisopropyl ether, ethylene glycol monobutyl ether, propylene glycol, propylene glycol monoacetate, propylene glycol monomethyl ether, propylene glycol-tert-butyl ether, dipropylene glycol monomethyl ether, diethylene glycol, diethylene glycol monoacetate, diethylene glycol dimethyl ether, dipropylene glycol monoacetate monomethyl ether, dipropylene glycol monomethyl ether, dipropylene glycol monoethyl ether, dipropylene glycol monoacetate monoethyl ether, dipropylene glycol monopropyl ether, dipropylene glycol monoacetate monopropyl ether, 3-methyl-3-methoxybutyl acetate, tripropylene glycol methyl ether, 3-methyl-3-methoxybutanol, diisopropyl ether, ethyl isobutyl ether, diisobutylene, amyl acetate, butyl butyrate, butyl ether, diisobutyl ketone, methylcyclohexene, propyl ether, dihexyl ether, 1-hexanol, n-hexane, n-pentane, n-octane, diethyl ether, methyl lactate, ethyl lactate, methyl acetate, ethyl acetate, n-butyl acetate, propylene glycol monoethyl ether acetate, methyl pyruvate, ethyl pyruvate, methyl 3-methoxypropionate, methylethyl 3-ethoxypropionate, ethyl 3-methoxypropionate, 3-ethoxypropionic acid, 3-methoxypropionic acid, propyl 3-methoxypropionate, butyl 3-methoxypropionate, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy)propanol, methyl lactate, ethyl lactate, n-propyl lactate, n-butyl lactate or isoamyl lactate.

Such poor solvents may be used alone or as a mixture of two or more. In a case where such a solvent is used, the proportion is preferably from 5 to 80 mass %, more preferably from 20 to 60 mass % to the total amount of the solvents contained in the liquid crystal aligning agent.

The compound to improve the film thickness uniformity or the surface smoothness may, for example, be a fluorinated surfactant, a silicone surfactant or a nonionic surfactant.

More specifically, for example, Eftop EF301, EF303 or EF352 (manufactured by TOHKEM PRODUCTS CORPORATION), MEGAFAC F171, F173 or R-30 (manufactured by DIC Corporation), Fluorad FC430 or FC431 (manufactured by Sumitomo 3M Limited) or AsahiGuard AG710, SURFLON S-382, SC101, SC102, SC103, SC104, SC105 or SC106 (manufactured by Asahi Glass Company, Limited) may be mentioned. The proportion of such a surfactant is preferably from 0.01 to 2 parts by mass, more preferably from 0.01 to 1 part by mass per 100 parts by mass of the resin components contained in the liquid crystal aligning agent.

As specific examples of the compound to improve the adhesion between the liquid crystal alignment film and the substrate, the following functional silane-containing compounds or epoxy group-containing compounds may, for example, be mentioned.

For example, 3-aminopropyltrimethoxysilane, 3-aminopropyltriethoxysilane, 2-aminopropyltrimethoxysilane, 2-aminopropyltriethoxysilane, N-(2-aminoethyl)-3-aminopropyltrimethoxysilane, N-(2-aminoethyl)-3-aminopropylmethyldimethoxysilane, 3-ureidopropyltrimethoxysilane, 3-ureidopropyltriethoxysilane, N-ethoxycarbonyl-3-aminopropyltrimethoxysilane, N-ethoxycarbonyl-3-aminopropyltriethoxysilane, N-triethoxysilylpropyl triethylene triamine, N-trimethoxysilylpropyl triethylene triamine, 10-trimethoxysilyl-1,4,7-triazadecane, 10-triethoxysilyl-1,4,7-triazadecane, 9-trimethoxysilyl-3,6-diazanonyl acetate, 9-triethoxysilyl-3,6-diazanonyl acetate, N-benzyl-3-aminopropyltrimethoxysilane, N-benzyl-3-aminopropyltriethoxysilane, N-phenyl-3- aminopropyltrimethoxysilane, N-phenyl-3-aminopropyltriethoxysilane, N-bis(oxyethylene)-3-aminopropyltrimethoxysilane, N-bis(oxyethylene)-3-aminopropyltriethoxysilane, ethylene glycol diglycidyl ether, polyethylene glycol diglycidyl ether, propylene glycol diglycidyl ether, tripropylene glycol diglycidyl ether, polypropylene glycol diglycidyl ether, neopentyl glycol diglycidyl ether, 1,6-hexanediol diglycidyl ether, glycerin diglycidyl ether, 2,2-dibromoneopentyl glycol diglycidyl ether, 1,3,5,6-tetraglycidyl-2,4-hexanediol, N,N,N',N'-tetraglycidyl-m-xylenediamine, 1,3-bis(N,N-diglycidylaminomethyl)cyclohexane or N,N,N',N'-tetraglycidyl-4,4'-diaminodiphenylmethane may be mentioned.

Further, the following phenoplast type additive may be contained for the purpose of preventing a decrease in the electrical properties by backlight, in addition to an improvement in the adhesion between the substrate and the film. Specific phenoplast type additives are as follows, but such additives are not limited to the following structures.

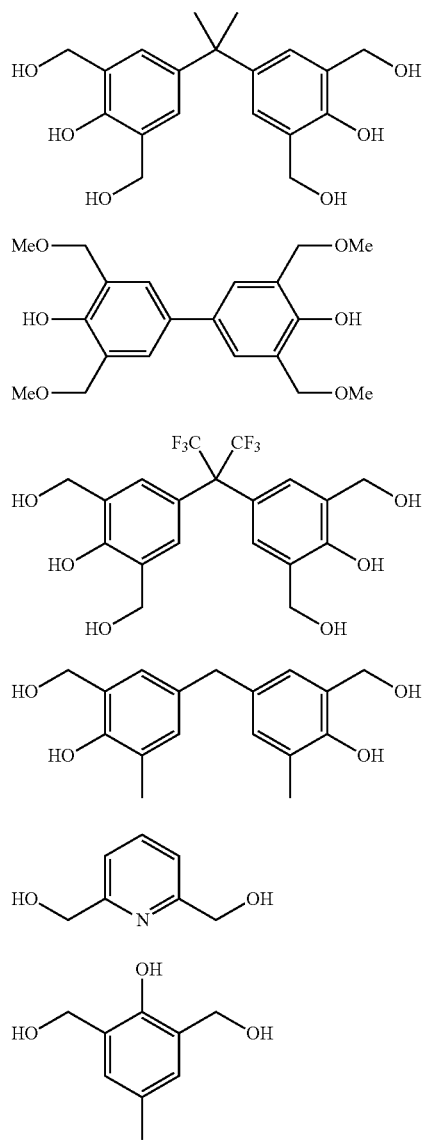

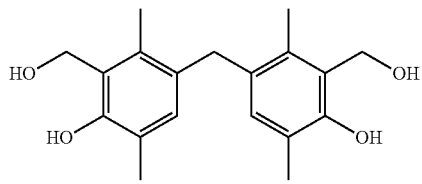

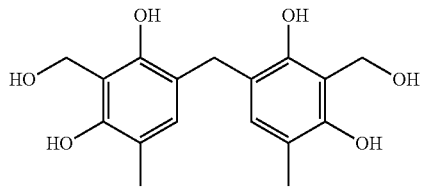

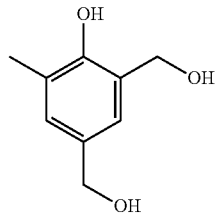

In a case where the compound to improve the adhesion with the substrate is used, its amount of use is preferably from 0.1 to 30 parts by mass, more preferably from 1 to 20 parts by mass per 100 parts by mass of the resin component contained in the liquid crystal aligning agent. If the amount of use is less than 0.1 part by mass, no effect to improve the adhesion will be expected, and if it is larger than 30 parts by mass, the alignment property of the liquid crystal may be deteriorated in some cases.

The liquid crystal aligning agent of the present invention may contain, in addition to the above compounds, a dielectric or an electrically conductive substance for the purpose of changing the electrical properties of the obtainable liquid crystal alignment film, such as the dielectric constant or the electrical conductivity, or a crosslinkable compound for the purpose of increasing the hardness and the denseness of a film when a liquid crystal alignment film is formed, within a range not to impair the effects of the present invention.

<Liquid Crystal Alignment Film/Liquid Crystal Display Device>

The liquid crystal aligning agent of the present invention is applied to a substrate and baked, followed by alignment treatment by e.g. rubbing treatment or irradiation with light, or without alignment treatment for e.g. application to vertical orientation, whereby a liquid crystal alignment film is obtained. On that occasion, the substrate used is not particularly limited so long as it is a highly transparent substrate, and a glass substrate or a plastic substrate such as an acrylic substrate or a polycarbonate substrate may, for example, be used. Further, it is preferred to use a substrate having ITO electrodes and the like to drive the liquid crystal formed thereon, from the viewpoint of simplification of the process.

Further, for a reflective liquid crystal display device, an opaque substrate such as a silicon wafer may be used only for a substrate on one side, and in such a case, as an electrode, a material which reflects light such as aluminum may be used.

The method of applying the liquid crystal aligning agent is not particularly limited, and industrially, it is common to employ screen printing, offset printing, flexographic printing or ink jet. As another application method, dipping, a roll coater, a slit coater or a spinner may, for example, be mentioned, and they may be employed depending upon the purpose.

The baking after the liquid crystal aligning agent is applied to the substrate is carried out at from 50 to 300° C., preferably from 80 to 250° C. by a heating means such as a hot plate to evaporate the solvent thereby to form a coating film. The thickness of the coating film formed after baking is preferably from 5 to 300 nm, more preferably from 10 to 100 nm, since if it is too thick, such is disadvantageous in view of the electric power consumption of a liquid crystal display device, and if it is too thin, the reliability of a liquid crystal display device may be lowered.

In the case of horizontal alignment or tilt alignment of the liquid crystal, the coating film after baking is treated e.g. by rubbing or irradiation with polarized ultraviolet rays.

The liquid crystal display device of the present invention is obtained by forming a substrate provided with a liquid crystal alignment film using the liquid crystal aligning agent of the present invention by the above means, and preparing a liquid crystal cell by a known means thereby to produce the liquid crystal display device.

As one example of preparation of the liquid crystal cell, a pair of substrates having a liquid crystal alignment film formed thereon is prepared, spacers are spread on the liquid crystal alignment film of one of the substrates, the other substrate is bonded so that the liquid crystal alignment film faces the inside, and the liquid crystal is vacuum injected, followed by sealing; or the liquid crystal is dropped on the liquid crystal alignment film on which spacers are spread, and then a substrate is bonded thereto for sealing. On that occasion, the thickness of the spacers is preferably from 1 to 30 μm, more preferably from 2 to 10 μm.

The liquid crystal display device prepared by using the liquid crystal aligning agent of the present invention as mentioned above is excellent in the reliability and is suitably used for e.g. large-sized and high precision liquid crystal televisions, etc.

EXAMPLES

Now, the present invention will be described in further detail with reference to Examples. However, it should be understood that the present invention is by no means restricted to such specific Examples.

Analysis methods used in Examples are as follows.
[1][Mass Spectrometric Analysis (MASS)]
Model: AQ-Tod (manufactured by JEOL Limited), ionization method: DART+, measurement range: m/z=100 to 1,000
[2] [1H NMR]
Model: NMR system 400 NB (400 MHz) manufactured by Varian
Measurement solvent: $CDCl_3$, $DMSO-d_6$
Standard substance: Tetramethylsilane (TMS)
[3] [Melting Point (m.p.)]
Model: Micro melting point measuring apparatus (MP-S3) (manufactured by Yanaco Kikikaihatsu Kenkyusho K. K.)

Example 1

Synthesis of 3,4-epoxy-tricyclo[5,2,1,0$^{2,6}$]decane-8,9-dicarboxylic acid anhydride

[ETC DA]
This compound was synthesized in accordance with the method disclosed in JP-A-60-156692.

Example 2

Synthesis of 2,3-epoxy-1-tetradecaoxymethyl-7-oxabicyclo[2.2.1]heptane-2,3-dicarboxylic acid anhydride (ETOA)

<Synthesis of TDF>

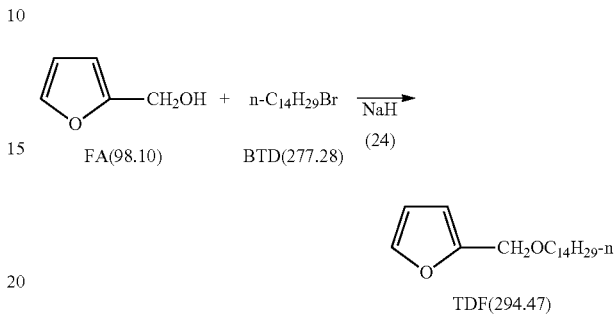

Into a 500 mL four-necked reaction flask, 29.4 g (300 mmol) of furfuryl alcohol (FA) and 206 g (7 times by mass) of N,N-dimethylformamide (DMF) were charged, and 14.4 g (330 mmol) of sodium hydride (purity: 55%) was added at an internal temperature of from 6° C. to 13° C. over a period of 1 hour with stirring by a magnetic stirrer under cooling with ice. Then, the ice bath was removed and the temperature was increased to room temperature (20° C.), and stirring was continued for 1 hour in the form of a slurry. Then, the flask was cooled again by an ice bath to an internal temperature of 5° C., and 87.3 g (315 mmol) of n-bromotetradecane was dropwise added over a period of 40 minutes. Further, the temperature was increased to 50° C., and stirring was continued for 18 hours. After completion of the reaction, the reaction liquid was concentrated under reduced pressure, and ethyl acetate and water were added to the obtained crude product under cooling with an ice bath, and 33 g of a 35 mass % hydrochloric acid was dropwise added with stirring, to acidify the solution. Then, an organic layer was isolated by liquid separation, washed with water and concentrated, to obtain 87.9 g of a dark red oily product. This oily product was purified by silica gel column chromatography (n-hexane/ethyl acetate=9/1 to 3/1 (v/v)) to obtain 66.8 g (yield: 75.6%) of an oily product.

This oily product was confirmed to be the desired 2-tetradecaoxymethylfuran (TDF) by MASS and $^1$H NMR.

MASS (ESI+, m/z(%)): 294.26 ([M]+, 100)

$^1$H NMR (CDCl3, δppm): 0.866-0.897 (m, 3H), 1.254-1.387 (m, 24H), 1.551-1.639 (m, 2H), 3.435-3.473 (m, 2H), 4.433 (d, J=1.2 Hz, 2H), 6.298-6.343 (m, 2H), 7.395-7.402 (m, 1H)

<Synthesis of TEEC>

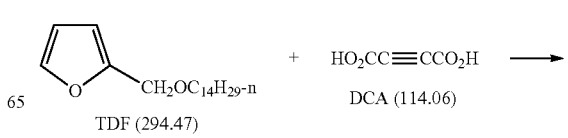

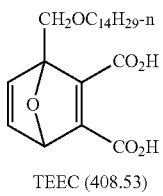

TEEC (408.53)

Into a 100 mL four-necked reaction flask, 11.6 g (39.4 mmol) of TDF, 5.7 g (50.0 mmol) of acetylenedicarboxylic acid and 74 g of 1,4-dioxane were charged, followed by stirring by a magnetic stirrer in an oil bath at 120° C. for 18 hours. Then, the reaction liquid was concentrated by a rotary evaporator, and n-heptane/ethyl acetate=9/1 (v/v) were added to the obtained residue for dissolution at 60° C., the reaction liquid was concentrated by a rotary evaporator, and a small amount of n-heptane was added, followed by cooling with ice, The precipitated crystals were collected by filtration, washed with n-heptane/ethyl acetate=9/1 (v/v) and vacuum dried at 50° C. to obtain 8.6 g (yield: 56%) of gray crystals.

The crystals were confirmed to be the desired 1-tetradecaoxymethyl-7-oxabicyclo[2.2.1]hepta-2,5-diene-5,6-dicarboxylic acid (TEEC) by MASS and $^1$H NMR. MASS (ESI+, m/z(%)): 409.2 ([M+H]+, 100)

$^1$H NMR (CDCl3, δppm): 0.866-0.895 (m, 3H), 1.255 (s, 24H), 1.595-1.644 (m, 2H), 3.592-3.789 (m, 2H), 4.179-4.241(m, 1H), 4.463 (d, J=11.6 Hz, 1H), 5.785 (t, J=2.0 Hz, 1H), 7.014 (t, J=2.8 Hz, 1H), 7.266-7.289 (m, 1H), 10.350 (brs, 2H) m.p.(° C.): 73-75

<Synthesis of ETEC>

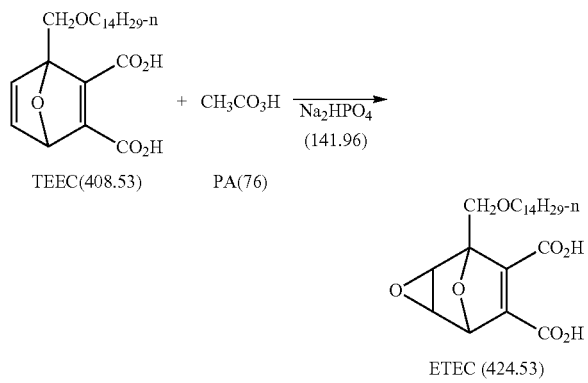

TEEC(408.53)  PA(76)

ETEC (424.53)

Into a 500 mL four-necked reaction flask, 19.5 g (47.7 mmol) of TEEC, 156 g (8 parts by mass) of 1,4-dioxane and 1.36 g of sodium phosphate were charged, followed by cooling to 12° C. in an ice bath, and 18.6 g (95.0 mmol) of peracetic acid (purity: 39%) was dropwise added with stirring by a magnetic stirrer. The ice bath was removed and the temperature was increased to room temperature, whereupon the reaction liquid slightly generated heat, and stirring was caried out at a temperature of 29° C. for 2 hours. Stirring was further caried out at 50° C. for 19 hours, and the reaction was terminated. Then, the reaction liquid was concentrated under reduced pressure to obtain 25 g of a yellow gummy product. 100 mL of ethyl acetate and 70 mL of water were added to the yellow gummy product, followed by heating for dissolution, and an organic layer was isolated by liquid separation. The organic layer was washed with 30 mL of water, concentrated and vacuum dried to obtain 20.5 g of a yellow gel. 77 g of acetonitrile was added to the yellow gel, followed by heating to 60° C., wehreupon a suspension was obtained, which was left at rest at 20° C. for 20 hours, whereby a solid content settled. The settled solid content was collected by filtration with cerite and vacuum dried to obtain 18.2 g (yield: 90%) of a red paste product.

This product was confirmed to be the desired 2,3-epoxy-1-tetradecaoxymethyl-7-oxabicyclo[2.2.1]hept-5-ene-5,6-dicarboxylic acid (ETEC) by MASS and $^1$H NMR. MASS (ESL m/z(%)): 423.5 ([M−H]−, 100)

$^1$H NMR (CDCl3, δppm): 0.878 (t, J=6.8 Hz, 3H), 1.287 (s, 24H), 1.578(s, 2H), 3.521-3.599 (m, 2H), 3.707 (d, J=19.2 Hz, 1H), 3.907 (d, J=32.8 Hz, 1H), 4.047 (d, J=12.8 Hz, 1H), 4.112 (d, J=9.2 Hz, 0.5H), 4.343 (d, J=11.6 Hz, 0.5H), 5.185 (d, J=1.6 Hz, 1H)

<Synthesis of ETAC>

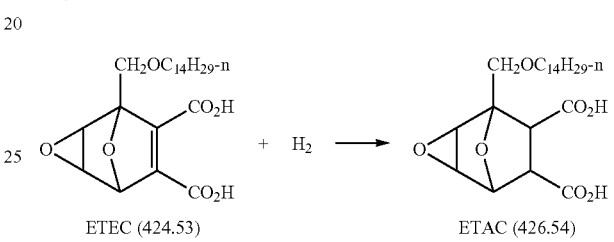

ETEC (424.53)  ETAC (426.54)

Into a 300 mL four-necked reaction flask, 18.0 g (42.4 mmol) of ETEC, 147 g (8 times by mass) of 1,4-dioxane and 4.03 g of a 5% Pd/C (moisture content: 55.99 mass %) were charged, and the atmosphere in the system was replaced with nitrogen, followed by stirring in a hydrogen atmosphere (baloon filled with hydrogen) under atmospheric pressure at from 25 to 27° C. for 54 hours. Then, the catalyst was removed by filtration with cerite, and the filtrate was concentrated to obtain 17.7 g of a red oily product. Then, 100 g of ethyl acetate and 40 g of water were added for dissolution, and the organic layer was concentrated and vacuum dried to obtain 15.6 g (yield: 86.5%) of a red oily product.

This product was confirmed to be the desired 2,3-epoxy-1-tetradecaoxymethyl-7-oxabicyclo[2.2.1]heptane-5,6-dicarboxylic acid (ETAC) by MASS and $^1$H NMR. MASS (ESI−, m/z(%)): 425.9 ([M−H]−, 100)

$^1$H NMR (CDCl3, δppm): 0.814 (t, J=6.4Hz, 3H), 1.197(s, 24H), 1.428(s, 2H), 2.741 (d, J=10.8 Hz, 0.5H), 3.001 (d, J=10.8 Hz, 0.5H), 3.176 (d, J=10.8 Hz, 0.5H), 3.253-3.307 (m, 1H), 3.342-3.422 (m, 0.5H), 3.684 (d, J=5.2 Hz, 1H), 3.772 (s, 1H), 4.189 (d, J=17.2 Hz, 1H), 4.389 (d, J=42.0 Hz, 1H), 4.474 (t, J=6.0 Hz, 1H), 5.316 (s, 1H)

<Synthesis of ETOA>

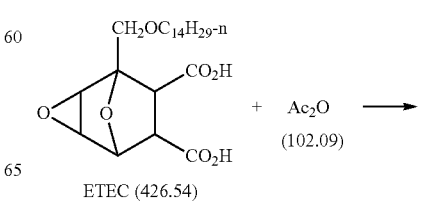

ETEC (426.54)

-continued

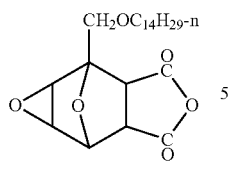
ETOA (408.53)

Into a 100 mL four-necked reaction flask, 15.6 g (36.6 mmol) of ETAC, 37.3 g (365 mmol) of acetic anhydride, 4.7 g of activated carbon and 125 g of toluene were charged, followed by stirring at an internal temperature of 71° C. (oil bath: 75° C.) for 2 hours and 30 minutes. Then, the reaction liquid was subjected to filtration with celite, concentrated and vacuum dried to obtain 13.1 g (yield: 82%) of a red oily product.

Then, 104 g of acetonitrile, 30.6 g (300 mmol) of acetic anhydride and 6.5 g of activatec carbon were charged to 13.0 g of the oily product, followed by stirring at an internal temperature of 71° C. (oil bath: 75° C.) for 3 hours. After completion of the reaction, the reaction liquid was cooled to 25° C., left at rest for one hour, subjected to filtration with celite, concentrated and vacuum dried to obtain 9.1 g (yield: 74%) of a pale orange oily product.

This product was confirmed to be the desired 2,3-epoxy-1-tetradecaoxymethyl-7-oxabicyclo[2.2.1]heptane-5,6-dicarboxylic acid anhydride (ETOA) by MASS and $^1$H NMR.

MASS (ESI$^-$, m/z(%)): 407.0 ([M–H]$^-$, 100)

$^1$H NMR (CDCl$_3$, δppm): 0.880 (t, J=6.8Hz, 3H), 1.299(s, 24H), 1.583-1.637(m, 2H), 2.010-2.301(m, 2H), 3.372-3.661 (m, 2H), 3.823-4.242 (m, 3H), 4.558-4.965 (m, 1H), 5.366 (s, 1H)

<Evaluation of Liquid Crystal Alignment Film Properties>

Abbreviations for compounds used for e.g. synthesis of the polyamic acid and the polyimide are as follows.

<Tetracarboxylic acid dianhydride>

CBDA: 1,2,3,4-cyclobutanetetracarboxylic acid dianhydride

TDA: 3,4-dicarboxy-1,2,3,4-tetrahydro-1-naphthalenesuccinic acid dianhydride

PMDA: pyromellitic acid dianhydride

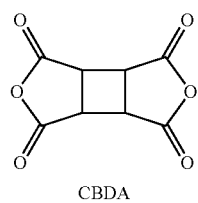
CBDA

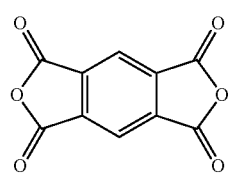
PMDA

-continued

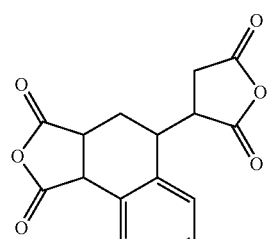
TDA

<Diamine> p-PDA: 1,4-phenylenediamine

DDM: 4,4-diaminodiphenylmethane

C18DAB: 4-octadecyloxy-1,3-diaminobenzene

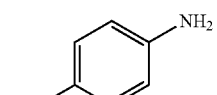
p-PDA

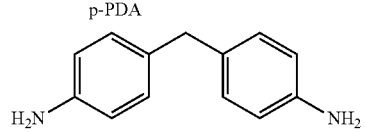
DDM

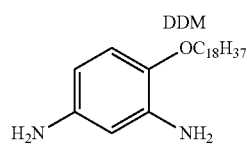
C18DAB

<Compounds having their Terminals Chemically Modified>

E-NDA: 2,3-epoxy-bicyclo(2,2,1)heptane-5,6-dicarboxylic acid anhydride

ETCDA: 3,4-epoxy-tricyclo[5.2.1.0$^{2,6}$]decane-8,9-dicarboxylic acid anhydride ETOA: 2,3-epoxy-1-tetradecaoxymethyl-7-oxabicyclo[2.2.1]heptane-5,6-dicarboxylic acid anhydride

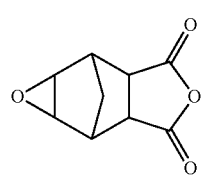
E-NDA

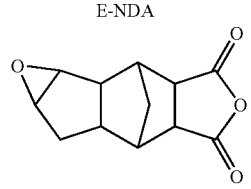
ETCDA

-continued

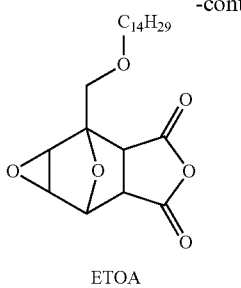
ETOA

<Organic Solvent>
NMP: N-methyl-2-pyrrolidone
γ-BL: γ-butyrolactone
BCS: butyl cellosolve <Measurement of Molecular Weight>

With respect to the molecular weight of the polymer obtained by the polymerization reaction, the number average molecular weight (Mn) and the weight average molecular weight (Mw) as values calculated as polyethylene glycol and polyethylene oxide, were calculated by measurement of the polyimide by a GPC (room temperature gel permeation chromatography) apparatus.

GPC apparatus: Shodex (GPC-101)
Column: Shodex (KD803 and KD805 in series)
Column temperature: 50° C.
Eluent: N,N-dimethylformamide (as additives, 30 mmol/L of lithium bromide monohydrate (LiBr-H$_2$O), 30 mmol/L of phosphoric acid anhydrous crystals (o-phosphoric acid) and 10 mL/L of tetrahydrofuran (THF))
Flow rate: 1.0 mL/min
Standard sample for preparation of analytical curve: TSK standard polyethylene oxide (molecular weight: about 900,000, 150,000, 100,000 and 30,000) manufactured by Tosoh Corporation and polyethylene glycol (molecular weight: about 12,000, 4,000 and 1,000) manufactured by Polymer Laboratories Ltd.

<Measurement of Imidization Degree>

The imidization degree of the polyimide in Synthesis Example was measured as follows.

20 mg of a polyimide powder was put in an NMR sample tube (NMR sampling tube standard manufactured by KUSANO SCIENCE CORPORATION), and 0.53 mL of deuterated dimethylsulfoxide (DMSO-d6, 0.05 mass % TMS mixture) was added, and ultrasonic waves were applied for complete dissolution. The solution was subjected to 500 MHz proton NMR measurement by an NMR measuring apparatus (JNW-ECA500) manufactured by JEOL Ltd. DATUM Solution Business Operations. The imidization degree was obtained in accordance with the following formula from the peak integrated value of proton derived from a structure which would not be changed as between before and after the imidization as standard proton, and the peak integrated value of proton derived from a NH group of the amide acid which appears in the vicinity of from 9.5 to 10.0 ppm.

Imidization degree (%)=(1−α·x/y)×100

In the above formula, x is the peak integrated value of proton derived from the NH group of the amide acid, y is the peak integrated value of standard proton, and α is the proportion of the number of standard proton per one proton of the NH group of the amide acid in the case of a polyamide acid (imidization degree of 0%).

Example 3

CBDA/p-PDA, polymerization of polyamic Acid having Amine Terminal Groups in Excess Into a 100 mL four-necked flask equipped with a mechanical stirrer and a nitrogen introduction tube, 5.41 g (50.0 mmol) of p-PDA and 81.8 g of dehydrated NMP were weighed, and p-PDA was completely dissolved while nitrogen was made to flow. Then, 9.02 g (46.0 mmol) of CBDA was slowly added under cooling with water, and reaction was carried out as it was for 6 hours to obtain a 15 mass % polyamic acid solution (PAA-1). The molecular weight of PAA-1 was 8300/18,700 (Mn/Mw).

Comparative Example 1

20.00 g of PAA-1 was weighed, and 15.0 g of NMP and 15.0 g BCS were added thereto for dilution to obtain a liquid crystal aligning agent (aligning agent 1) comprising 6 mass % of PAA-1, 64 mass % of NMP and 30 mass % of BCS.

Example 4

E-NDA-modified CBDA/p-PDA, Polymerization of Polyamic Acid

Into a 50 mL four-necked flask equipped with a mechanical stirrer and a nitrogen introduction tube, 20.0 g of PAA-1 was weighed, and 0.19 g (1.03 mmol, about 0.10 molar equivalent to p-PDA) of E-NDA (Mw: 180.16 g/mol) was added, and reaction was carried out at room temperature for 24 hours to obtain PAA-2.

15.0 g of NMP and 15.0 g of BCS were added to the solution for dilution to obtain a liquid crystal aligning agent (aligning agent 2) comprising about 6.0 mass % of PAA-2, 64 mass % of NMP and 30 mass % of BCS.

Example 5

ETCDA-Modified CBDA/p-PDA, Polymerization of Polyamic Acid

Into a 50 mL four-necked flask equipped with a mechanical stirrer and a nitrogen introduction tube, 20.0 g of PAA-1 was weighed, and 0.22 g (1.03 mmol, about 0.10 molar equivalent to p-PDA) of ETCDA (Mw: 220.22 g/mol) was added, and reaction was carried out at room temperature for 24 hours to obtain PAA-3.

15.0 g of NMP and 15.0 g of BCS were added to the solution for dilution to obtain a liquid crystal aligning agent (aligning agent 3) comprising about 6.0 mass % of PAA-3, 64 mass % of NMP and 30 mass % of BCS.

Example 6

ETOA-Modified CBDA/p-PDA, Polymerization of Polyamic Acid

Into a 50 mL four-necked flask equipped with a mechanical stirrer and a nitrogen introduction tube, 20.0 g of PAA-1 was weighed, and 0.42 g (1.03 mmol, about 0.10 molar equivalent to p-PDA) of ETOA (Mw: 408.53 g/mol) was added, and reaction was carried out at room temperature for 24 hours to obtain PAA-4.

15.0 g of NMP and 15.0 g of BCS were added to the solution for dilution to obtain a liquid crystal aligning agent (aligning agent 4) comprising about 6.0 mass % of PAA-4, 64 mass % of NMP and 30 mass % of BCS.

Example 7

CBDA/DDM, Polymerization of Polyamic Acid having Amine Terminal Groups in Excess Into a 200 mL four-necked flask equipped with a mechanical stirrer and a nitrogen introduction tube, 9.91 g (50.0 mmol) of DDM and 107.3 g of dehydrated NMP were weighed, DDM was completely dissolved while nitrogen was made to flow, 9.02 g (46.0 mmol) of CBDA was slowly added under cooling with water, and reaction was carried out as it was for 6 hours to obtain a 15 mass % polyamic acid solution (PAA-5). The molecular weight of PAA-5 was 9500/21400 (Mn/Mw).

Comparative Example 2

20.00 g of PAA-A was weighed, and 15.0 g of NMP and 15.0 g BCS were added thereto for dilution to obtain a liquid crystal aligning agent (aligning agent 5) comprising 6 mass % of PAA-5, 64 mass % of NMP and 30 mass % of BCS.

Example 8

E-NDA-Modified CBDA/DDM, Polymerization of Polyamic Acid

Into a 50 mL four-necked flask equipped with a mechanical stirrer and a nitrogen introduction tube, 20.0 g of PAA-5 was weighed, and 0.19 g (1.03 mmol, about 0.10 molar equivalent to DDM) of E-NDA (Mw: 180.16 g/mol) was added, and reaction was carried out at room temperature for 24 hours to obtain PAA-6.

15.0 g of NMP and 15.0 g of BCS were added to the solution for dilution to obtain a liquid crystal aligning agent (aligning agent 6) comprising about 6.0 mass % of PAA-6, 64 mass % of NMP and 30 mass % of BCS.

Example 9

ETCDA-Modified CBDA/DDM, Polymerization of Polyamic acid

Into a 50 mL four-necked flask equipped with a mechanical stirrer and a nitrogen introduction tube, 20.0 g of PAA-5 was weighed, and 0.22 g (1.03 mmol, about 0.10 molar equivalent to DDM) of ETCDA (Mw: 220.22 g/mol) was added, and reaction was carried out at room temperature for 24 hours to obtain PAA-7.

15.0 g of NMP and 15.0 g of BCS were added to the solution for dilution to obtain a liquid crystal aligning agent (aligning agent 7) comprising about 6.0 mass % of PAA-7, 64 mass % of NMP and 30 mass % of BCS.

Example 10

ETOA-Modified CBDA/DDM, Polymerization of Polyamic Acid

Into a 50 mL four-necked flask equipped with a mechanical stirrer and a nitrogen introduction tube, 20.0 g of PAA-5 was weighed, and 0.42 g (1.03 mmol, about 0.10 molar equivalent to DDM) of ETOA (Mw: 408.53 g/mol) was added, and reaction was carried out at room temperature for 24 hours to obtain PAA-8.

15.0 g of NMP and 15.0 g of BCS were added to the solution for dilution to obtain a liquid crystal aligning agent (aligning agent 8) comprising about 6.0 mass % of PAA-8, 64 mass % of NMP and 30 mass % of BCS.

Example 11

TDA/p-PDA, C18DAB(10), Polymerization of Polyamic Acid having Amine Terminal Groups in Excess Into a 50 mL side arm flask equipped with a stirrer and a nitrogen introduction tube, 4.50 g (15.0 mmol) of TDA and 25.6 g of dehydrated NMP were weighed, 1.88 g (5.00 mmol) of C18DAB was added while nitrogen was made to flow, and reaction was carried out at 40° C. for 3 hours.

Into a 200 mL four-necked flask equipped with a mechanical stirrer and a nitrogen introduction tube, 4.87 g (45.0 mmol) of p-PDA and 93.4 g of dehydrated NMP were weighed, p-PDA was completely dissolved while nitrogen was made to flow, and the above-prepared reaction solution and 9.76 g (32.5 mmol) of TDA were slowly added thereto under cooling with water, and reaction was carried out at 40° C. for 16 hours to obtain a 15 mass % polyamic acid solution (PAA-9). The molecular weight of PAA-5 was 8500/20300 (Mn/Mw).

Example 12

TDA/p-PDA, C18DAB(10), Synthesis of Polyimide

Into a 100 mL eggplant flask in which a stirrer was put, 30.0 g of PAA-9 was weighed, 45.0 g of NMP, 10.9 g (106.8 mmol) of acetic anhydride and 5.08 g (64.2 mmol) of pyridine were added, followed by stirring at room temperature for 30 minutes, and reaction was carried out at 40° C. for 3 hours. After the reaction, the reaction solution was slowly poured to 300 mL of methanol cooled to about 10° C. with stirring to precipitate a solid. The precipitated solid was recovered by filtration, and further dispersed and washed twice with 200 ml of methanol, and then dried at 100° C. for 12 hours to obtain polyimide (SPI-1). The molecular weight of SPI-1 was 7900/18500 (Mn/Mw), and the imidization degree was 84%.

Into a 100 mL eggplant flask in which a stirrer was put, 3.0 g of SPI-1 was weighed, 34.5 g of γ-BL was added, followed by stirring at 50° C. for 16 hours for dissolution, and 12.5 g of γ-BL was further added to obtain a polyimide solution (SPI-1S) comprising 6 mass % of SPI-1 and 94 mass % of γ-BL.

Example 13

E-NDA-Modified TDA/p-PDA, C18DAB(10), Synthesis of Polyimide

Into a 100 mL eggplant flask in which a stirrer was put, 30.0 g of PAA-9 was weighed, 0.19 g (1.07 mmol, about 0.10 molar equivalent to diamine) of E-NDA (Mw: 180.16 g/mol) was added, reaction was carried out at 40° C. for 6 hours, 45.0 g of NMP, 10.9 g (106.8 mmol) of acetic anhydride and 5.08 g (64.2 mmol) of pyridine were added, followed by stirring at room temperature for 30 minutes, and reaction was carried out at 40° C. for 3 hours. After the reaction, the reaction solution was slowly poured to 300 mL of methanol cooled to about 10° C. with stirring to precipitate a solid. The precipitated solid was recovered by filtration, and further dispersed and washed twice with 200 ml of methanol, and then dried at 100° C. for 12 hours to obtain polyimide (SPI-2). The molecular weight of SPI-2 was 8400/19200 (Mn/Mw), and the imidization degree was 87%.

Into a 100 mL eggplant flask in which a stirrer was put, 3.0 g of SPI-2 was weighed, 34.5 g of γ-BL was added, followed by stirring at 50° C. for 16 hours for dissolution, and 12.5 g of γ-BL was further added to obtain a polyimide solution (SPI-2S) comprising 6 mass % of SPI-1 and 94 mass % of γ-BL.

Example 14

ETCDA-Modified TDA/p-PDA, C18DAB(10), Synthesis of Polyimide

Into a 100 mL eggplant flask in which a stirrer was put, 30.0 g of PAA-9 was weighed, 0.23 g (1.07 mmol, about 0.10 molar equivalent to diamine) of ETCDA (Mw: 220.22 g/mol) was added, reaction was carried out at 40° C. for 6 hours, 45.0 g of NMP, 10.9 g (106.8 mmol) of acetic anhydride and 5.08 g (64.2 mmol) of pyridine were added, followed by stirring at room temperature for 30 minutes, and reaction was carried out at 40° C. for 3 hours. After the reaction, the reaction solution was slowly poured to 300 mL of methanol cooled to about 10° C. with stirring to precipitate a solid. The precipitated solid was recovered by filtration, and further dispersed and washed twice with 200 ml of methanol, and then dried at 100° C. for 12 hours to obtain polyimide (SPI-3). The molecular weight of SPI-3 was 7900/18800 (Mn/Mw), and the imidization degree was 88%.

Into a 100 mL eggplant flask in which a stirrer was put, 3.0 g of SPI-2 was weighed, 34.5 g of γ-BL was added, followed by stirring at 50° C. for 16 hours for dissolution, and 12.5 g of γ-BL was further added to obtain a polyimide solution (SPI-3S) comprising 6 mass % of SPI-1 and 94 mass % of γ-BL.

Example 15

ETOA-Modified TDA/p-PDA, C18DAB(10), Synthesis of Polyimide

Into a 100 mL eggplant flask in which a stirrer was put, 30.0 g of PAA-9 was weighed, 0.44 g (1.07 mmol, about 0.10 molar equivalent to diamine) of ETOA (Mw: 408.53 g/mol) was added, reaction was carried out at 40° C. for 6 hours, 45.0 g of NMP, 10.9 g (106.8 mmol) of acetic anhydride and 5.08 g (64.2 mmol) of pyridine were added, followed by stirring at room temperature for 30 minutes, and reaction was carried out at 40° C. for 3 hours. After the reaction, the reaction solution was slowly poured to 300 mL of methanol cooled to about 10° C. with stirring to precipitate a solid. The precipitated solid was recovered by filtration, and further dispersed and washed twice with 200 ml of methanol, and then dried at 100° C. for 12 hours to obtain polyimide (SPI-4). The molecular weight of SPI-4 was 8200/19100 (Mn/Mw), and the imidization degree was 85%.

Into a 100 mL eggplant flask in which a stirrer was put, 3.0 g of SPI-2 was weighed, 34.5 g of γ-BL was added, followed by stirring at 50° C. for 16 hours for dissolution, and 12.5 g of γ-BL was further added to obtain a polyimide solution (SPI-4S) comprising 6 mass % of SPI-1 and 94 mass % of γ-BL.

Example 16

CBDA, PMDA(50)/DDM, Polymerization of Polyamic Acid

Into a 300 mL four-necked flask equipped with a mechanical stirrer and a nitrogen introduction tube, 19.83 g (100.0 mmol) of DDM, 111.0 g of dehydrated NMP and 111.0 g of γ-BL were weighed, DDM was completely dissolved while nitrogen was made to flow, and 10.91 g (50.0 mmol) of PMDA and 8.43 g (43.0 mmol) of CBDA were slowly added under cooling with water, and reaction was carried out as it was for 6 hours to obtain a 15 mass % polyamic acid solution (PAA-10). The molecular weight of PAA-10 was 10100/21400 (Mn/Mw).

Into a 1 L eggplant flask in which a stirrer was put, 250.0 g of PAA-10 was weighed, and 281.3 g of γ-BL and 93.8 g of BCS were added for dilution to obtain a polyamic acid solution (PAA-10S) comprising 6 mass % of PAA-10, 17 mass % of NMP, 62 mass % of γ-BL and 15 mass % of BCS.

Comparative Example 3

Into a 300 mL eggplant flask in which a stirrer was put, 40.0 g of the polyimide solution (SPI-1S) prepared in Example 12 and 160 g of the polyamic acid solution (PAA-10) prepared in Example 16 were added, followed by stirring for 24 hours to obtain a liquid crystal aligning agent (aligning agent 9) comprising 1.2 mass % of SPI-1, 4.8 mass % of PAA-10, 14 mass % of NMP, 68 mass % of γ-BL and 12 mass % of BCS.

Example 17

A liquid crystal aligning agent (aligning agent 10) was obtained in the same manner as in Comparative Example 3 using the polyimide solution SPI-2S.

Example 18

A liquid crystal aligning agent (aligning agent 11) was obtained in the same manner as in Comparative Example 3 using the polyimide solution SPI-3S.

Example 19

A liquid crystal aligning agent (aligning agent 12) was obtained in the same manner as in Comparative Example 3 using the polyimide solution SPI-3S.

<Preparation of Liquid Crystal cell>

A liquid crystal cell was prepared as follows using each of the liquid crystal aligning agents prepared in Examples and Comparative Examples.

The liquid crystal aligning agent was spin-coated on a glass substrate provided with transparent electrodes, dried for 70 seconds on a hot plate of 80° C. and then baked for 10 minutes on a hot plate of 220° C. to form a coating film having a thickness of 100 nm. With respect to the liquid crystal alignment treatment by rubbing, the coated surface was subjected to rubbing by means of a rayon cloth (YA-20R manufactured by Kikkawakakou K. K.) by a rubbing apparatus having a roll diameter of 120 mm under conditions of a roll rotational speed of 1,000 rpm, a roll advancing speed of 50 mm/sec and a pushing amount of 0.3 mm, to obtain a substrate provided with a liquid crystal alignment film.

Further, in evaluation of the rubbing resistance, observation was carried out by a confocal laser scanning microscope (manufactured by Lasertec Corporation, real time laser scanning microscope 1 LM21D) ("VL2000" manufactured by Lasertec Corporation) with a pushing amount of 0.5 mm.

Two sheets of the above substrate provided with a liquid crystal alignment film subjected to the liquid crystal alignment treatment, were prepared, spacers of 6 μm were spread on the liquid crystal alignment film of one sheet, then a sealing agent was printed thereon, and the other substrate was bonded so that the liquid crystal alignment film surfaces faced each other and that their rubbing directions were at right angles with each other (twisted nematic liquid crystal cell), whereupon the sealing agent was cured to prepare a void cell. To this void cell, liquid crystal MLC-2003 (manufactured by Merck Japan Limited) was injected by a reduced pressure injection method, and the injection inlet was sealed to obtain a twisted nematic liquid crystal cell.

Methods for measuring physical properties of each prepared liquid crystal cell and methods for evaluating the properties are as follows.

<Evaluation of Rubbing Resistance>

As a verification test for the rubbing resistance, rubbing was caried out under conditions with a pushing amount of 0.5 mm, and the film surface was observed by a comfocal laser scaning microscope. Evaluation was made under the folowing standards.

○: No scrapes or rubbing scars observed.
Δ: Scrapes or rubbing scars observed.
×: The film peeled or rubbing scars visually observed.

<Measurement of Pretilt Angle>

The prepared twisted nematic liquid crystal cell was heated at 105° C. for 5 minutes, and the pretilt angle and the voltage retention were measured. The pretilt angle was measured by Axo Scan (Mueller Matrix Polarimeter) manufactured by Axometorics, Inc.

<Measurement of Voltage Retention between before and after Backlight Aging Test>

To measure the voltage retention of the prepared twisted nematic liquid crystal cell, a voltage of 4 V was applied at a temperature of 90° C. for 60 μs, and the voltage 16.67 ms later was measured, whereupon the degree how the voltage was retained was calculated as the voltage retention.

Further, after completion of the measurement, the liquid crystal cell was left to stand for 3 weeks on a backlight module for a 40 inch liquid crystal TV, whereupon the voltage retention was measured, and the rate of change was estimated. To measure the voltage retention (VHR), a voltage retention measuring apparatus VHR-1 manufactured by TOYO Corporation was used, and the rate of change between before and after aging was calculated in accordance with the following formula.

(Calculation formula for rate of change)

Rate of change of VHR [%]=[1−(VHR after aging/VHR before aging)]×100

In Tables 2 and 3, the aligning agent means the liquid crystal aligning agent.

TABLE 1

| Examples | Polymer | Tetracarboxylic acid dianhydride | Diamine | Terminal-modified acid anhydride |
|---|---|---|---|---|
| 3 | PAA-1 | CBDA (0.92) | p-PDA (1.00) | — |
| 4 | PAA-2 | CBDA (0.92) | p-PDA (1.00) | E-NDA |
| 5 | PAA-3 | CBDA (0.92) | p-PDA (1.00) | ETCDA |
| 6 | PAA-4 | CBDA (0.92) | p-PDA (1.00) | ETOA |
| 7 | PAA-5 | CBDA (0.92) | DDM (1.00) | — |
| 8 | PAA-6 | CBDA (0.92) | DDM (1.00) | E-NDA |
| 9 | PAA-7 | CBDA (0.92) | DDM (1.00) | ETCDA |
| 10 | PAA-8 | CBDA (0.92) | DDM (1.00) | ETOA |
| 11 | PAA-9 | TDA (0.95) | p-PDA (0.90) C18DAB (0.10) | — |
| 12 | SPI-1 | TDA (0.95) | p-PDA (1.00) C18DAB (0.10) | — |
| 13 | SPI-2 | TDA (0.93) | p-PDA (1.00) C18DAB (0.10) | E-NDA |
| 14 | SPI-3 | TDA (0.93) | p-PDA (1.00) C18DAB (0.10) | ETCDA |
| 15 | SPI-4 | TDA (0.93) | p-PDA (1.00) C18DAB (0.10) | ETOA |
| 16 | PAA-10 | CBDA (0.43) PMDA (0.50) | DDM (1.00) | — |

TABLE 2

| Examples | Aligning agent | Polymer | Solvent | | |
|---|---|---|---|---|---|
| Comp. Ex. 1 | 1 | PAA-1 (6) | NMP (64) | BCS (30) | — |
| 4 | 2 | PAA-2 (6) | NMP (64) | BCS (30) | — |
| 5 | 3 | PAA-3 (6) | NMP (64) | BCS (30) | — |
| 6 | 4 | PAA-4 (6) | NMP (64) | BCS (30) | — |
| Comp. Ex. 2 | 5 | PAA-5 (6) | NMP (64) | BCS (30) | — |
| 8 | 6 | PAA-6 (6) | NMP (64) | BCS (30) | — |
| 9 | 7 | PAA-7 (6) | NMP (64) | BCS (30) | — |
| 10 | 8 | PAA-8 (6) | NMP (64) | BCS (30) | — |
| Comp. Ex. 3 | 9 | SPI-1 (1.2) PAA-10 (4.8) | γ-BL (68) | NMP (14) | BCS (12) |
| 17 | 10 | SPI-2 (1.2) PAA-10 (4.8) | γ-BL (68) | NMP (14) | BCS (12) |
| 18 | 11 | SPI-3 (1.2) PAA-10 (4.8) | γ-BL (68) | NMP (14) | BCS (12) |
| 19 | 12 | SPI-4 (1.2) PAA-10 (4.8) | γ-BL (68) | NMP (14) | BCS (12) |

TABLE 3

| | | | VHR | | |
|---|---|---|---|---|---|
| Aligning agent | Rubbing resistance | Pretilt angle [°] | 90° C. Initial | 90° C. BL aging | Rate of change of VHR [%] |
| 1 (Comp. Ex. 1) | ×-Δ | 2 | 84.9 | 80.3 | 5.4 |
| 2 | ○ | 2.2 | 86.2 | 82.6 | 4.2 |
| 3 | ○ | 2.1 | 88.3 | 84.7 | 4 |
| 4 | Δ-○ | 53.3 | 84.8 | 81.2 | 4.2 |

TABLE 3-continued

| Aligning agent | Rubbing resistance | Pretilt angle [°] | VHR 90° C. Initial | VHR 90° C. BL aging | Rate of change of VHR [%] |
|---|---|---|---|---|---|
| 5 (Comp. Ex. 2) | Δ | 1.8 | 92.2 | 90.4 | 2 |
| 6 | ○ | 1.8 | 93.3 | 92 | 1.4 |
| 7 | ○ | 1.9 | 93.5 | 92.1 | 1.4 |
| 8 | ○ | 63.8 | 92.1 | 90.7 | 1.5 |
| 9 (Comp. Ex. 3) | Δ | 3.1 | 95.4 | 93.3 | 2.2 |
| 10 | ○ | 3.4 | 95.5 | 94.1 | 1.2 |
| 11 | ○ | 3.4 | 95.4 | 94.4 | 1 |
| 12 | ○ | 4.2 | 95.4 | 93.5 | 2.1 |

In Table 3, with each of the liquid crystal aligning agents 2 to 4, 6 to 8 and 10 to 12 which are Examples of the present invention, the rubbing resistance was improved, and an effect to impart the pretilt angle was confirmed in the case of TEOA with a side chain. Further, an effect to suppress a decrease in VHR after backlight aging was also observed, although no effect to improve VHR was observed.

INDUSTRIAL APPLICABILITY

The polyimide precursor and/or polyimide having its terminal chemcially modified with the alicyclic epoxydicarboxylic acid anhydride of the present invention is suitably used, for exmaple, as a protective material for a liquid crystal display device or a semiconductor, an electronic material such as an insulating material, or a material for optical communication such as a light waveguide. Particularly, when it is used for a liquid crystal aligning agent, it is posible to prepare a liquid crystal display device with high reliability, and it is suitably used for e.g. a TN liquid crystal display device, a STN liquid crystal display device, a TFT liquid crystal display device, a VA liquid crystal display device, an IPS liquid crystal display device or an OCB liquid crystal display device.

The entire disclosure of Japanese Patent Application No. 2011-101814 filed on Apr. 28, 2011 including specification, claims and summary is incorporated herein by reference in its entirety.

The invention claimed is:

1. A polyimide precursor, having its terminal amino group modified with at least one alicyclic epoxydicarboxylic acid anhydride selected from the group consisting of a compound of formulae [1] and a compound of formula [2], or a polyimide thereof:

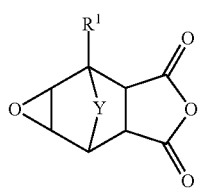

[1]

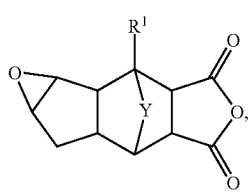

[2]

R1 = H, or —$X^1$—$X^2$—$X^3$ wherein:

Y is a $C_{1-2}$ alkylene or an oxygen atom;

$R^1$ is a hydrogen atom or an organice group represented by —$X^1$—$X^2$—$X^3$;

$X^1$ is a single bond or —$CH_2$—;

$X^2$ is a single bond or —O—; and $X^3$ is a $C_{1-20}$ alkyl group, a $C_{1-20}$ haloalkyl group or a $C_{1-20}$ alkyl group containing a cyano group.

2. The polyimide precursor or polyimide according to claim 1, wherein the alicyclic epoxydicarboxylic acid anhydride is at least one compound selected from the group consisting of a compound represented by formula [A], a compound represented by formula [B], and a compound represented by formula [C]:

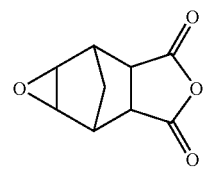

[A]

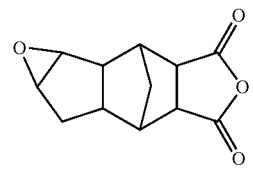

[B]

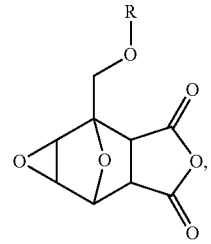

[C]

wherein R is a $C_{1-20}$ alkyl group, a $C_{1-20}$ haloalkyl group or a $C_{1-20}$ alkyl group containing a cyano group.

3. A liquid crystal aligning agent, comprising at least one of the polyimide precursor, or the polyimide obtained by imidizing the polyimide precursor according to claim 2.

4. A liquid crystal aligning agent, comprising at least one of the polyimide precursor, or the polyimide obtained by imidizing the polyimide precursor according to claim 1.

5. A liquid crystal alignment film obtained from the liquid crystal aligning agent of claim 4.

6. A liquid crystal display device, comprising the liquid crystal alignment film of claim 5.

7. A method for producing a polyimide precursor having its terminal amino group modified, the method comprising reacting at least one alicyclic epoxydicarboxylic acid anhydride selected from the group consisting of a compound of formulae [1] and a compound of [2] with a polyimide precursor having an amino group at its terminal:

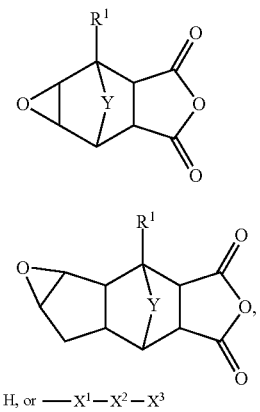

R1 = H, or —X¹—X²—X³ wherein:

Y is a $C_{1-2}$ alkylene or an oxygen atom;

$R^1$ is a hydrogen atom or an organic group represented by —X¹—X²—X³;

$X^1$ is a single bond or —CH$_2$—;

$X^2$ is a single bond or —O—; and $X^3$ is a $C_{1-20}$ alkyl group, a $C_{1-20}$ haloalkyl group or a $C_{1-20}$ alkyl group containing a cyano group; and wherein said polymide precursor is a polyamic acid or a polyamic acid ester.

8. The method according to claim 7, wherein the polyimide precursor is a polyimide precursor having from 50 to 100% of its terminal amino groups, relative to the total number of terminal groups, derived from a tetracarboxylic acid and a diamine.

9. A method for producing a polyimide having its terminal amino group modified, the method comprising imidizing a polyimide precursor selected from the group consisting of a polyamic acid or a polyamic acid ester to obtain a polyimide, reacting the polyimide with at least one alicyclic epoxydicarboxylic acid anhydride selected from the group consisting of a compound of formulae [1] and a compound of [2] with a polyimide precursor having an amino group at its terminal:

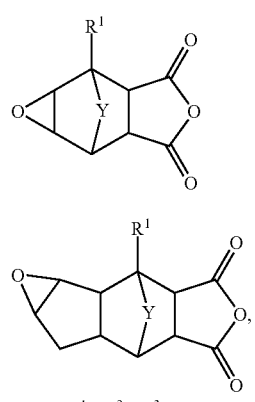

R1 = H, or —X¹—X²—X³ wherein:

Y is a $C_{1-2}$ alkylene or an oxygen atom;

$R^1$ is a hydrogen atom or an organic group represented by —X¹—X²—X³;

$X^1$ is a single bond or —CH$_2$—;

$X^2$ is a single bond or —O—; and $X^3$ is a $C_{1-20}$ alkyl group, a $C_{1-20}$ haloalkyl group or a $C_{1-20}$ alkyl group containing a cyano group.

10. The method according to claim 9, wherein the polyimide precursor is a polyimide precursor having from 50 to 100% of its terminal amino groups, relative to the total number of terminal groups, derived from a tetracarboxylic acid and a diamine.

11. A compound represented by the formula [1]:

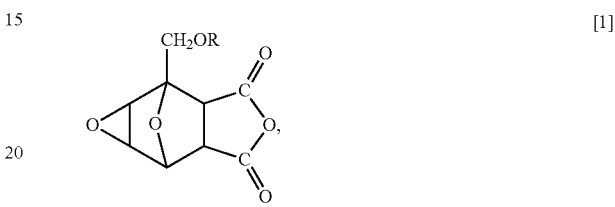

wherein R is a $C_{1-20}$ alkyl group, a $C_{1-20}$ haloalkyl group or a $C_{1-20}$ alkyl group containing a cyano group.

12. The compound according to claim 11, wherein R is a n-tetradecyl group.

13. A process for producing the compound of claim 11 represented by the formula [1]:

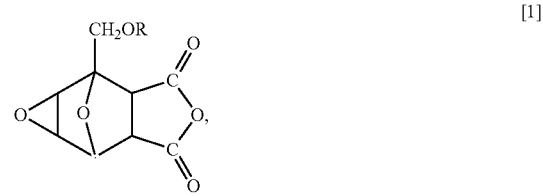

the process comprising:

reacting furfuryl alcohol with a substituted alkyl halide represented by the formula [4]:

RX   [4], wherein X is a halogen;

in the presence of a base to obtain a compound represented by the formula [5]:

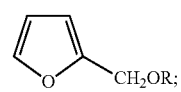

reacting the compound represented by the formula [5] with acetylenedicarboxylic acid to obtain a compound represented by the formula [6]:

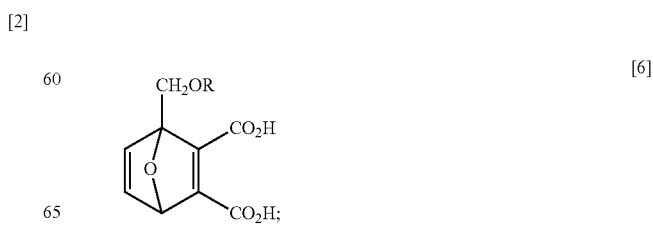

oxidizing the compound represented by the formula [6] to obtain a compound represented by the formula [3]:

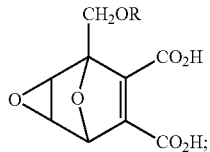

[3]

reducing the compound represented by the formula [3] to obtain a compound represented by the formula [2]:

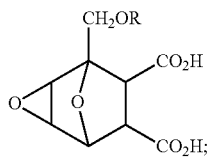

[2]

and
dehydrating the compound represented by formula [2] with a dehydrating agent to form the compound represented by formula [1],
wherein R is a $C_{1-20}$ alkyl group, a $C_{1-20}$ haloalkyl group or a $C_{1-20}$ alkyl group containing a cyano group.

14. The process according to claim 13, wherein R is a n-tetradecyl group.

15. A compound represented by the formula [2]:

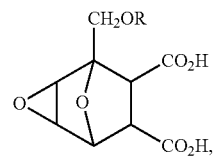

[2]

wherein R is a $C_{1-20}$ alkyl group, a $C_{1-20}$ haloalkyl group or a $C_{1-20}$ alkyl group containing a cyano group.

16. The compound according to claim 15, wherein R is a n-tetradecyl group.

17. A compound represented by the formula [3]:

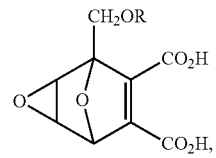

[3]

wherein R is a $C_{1-20}$ alkyl group, a $C_{1-20}$ haloalkyl group or a $C_{1-20}$ alkyl group containing a cyano group.

18. The compound according to claim 17, wherein R is a n-tetradecyl group.

* * * * *